United States Patent
Ruddock et al.

(10) Patent No.: US 9,892,229 B2
(45) Date of Patent: Feb. 13, 2018

(54) DIAGNOSIS AND RISK STRATIFICATION OF BLADDER CANCER

(71) Applicant: RANDOX LABORATORIES LTD., Crumlin (GB)

(72) Inventors: Mark William Ruddock, Crumlin (GB); Cherith N. Reid, Crumlin (GB); Kate E. Williamson, Belfast (GB); Frank Emmert-Streib, Belfast (GB); John V. Lamont, Crumlin (GB); Peter Fitzgerald, Crumlin (GB)

(73) Assignee: RANDOX LABORATORIES LTD. (GB)

( * ) Notice: Subject to any disclaimer, the term of this patent is extended or adjusted under 35 U.S.C. 154(b) by 41 days.

(21) Appl. No.: 14/435,991

(22) PCT Filed: Oct. 16, 2013

(86) PCT No.: PCT/GB2013/052705
§ 371 (c)(1),
(2) Date: Apr. 15, 2015

(87) PCT Pub. No.: WO2014/060753
PCT Pub. Date: Apr. 24, 2014

(65) Prior Publication Data
US 2015/0269311 A1 Sep. 24, 2015

(30) Foreign Application Priority Data
Oct. 16, 2012 (GB) .................................. 1218570.8

(51) Int. Cl.
*G01N 33/48* (2006.01)
*G06F 19/18* (2011.01)
(Continued)

(52) U.S. Cl.
CPC ....... *G06F 19/18* (2013.01); *G01N 33/57407* (2013.01); *G01N 33/57484* (2013.01); *G06F 19/24* (2013.01); *G06F 19/3431* (2013.01); *G01N 2333/475* (2013.01); *G01N 2333/4737* (2013.01); *G01N 2333/4742* (2013.01); *G01N 2333/485* (2013.01); *G01N 2333/523* (2013.01); *G01N 2333/525* (2013.01); *G01N 2333/545* (2013.01); *G01N 2333/5406* (2013.01); *G01N 2333/5412* (2013.01);
(Continued)

(58) Field of Classification Search
CPC ...... G01N 33/48; G01N 33/582; G06F 19/18; G06F 19/20; G06F 19/22; G06F 19/24
See application file for complete search history.

(56) References Cited

U.S. PATENT DOCUMENTS

| | | |
|---|---|---|
| 2009/0221010 A1 | 9/2009 | Elting et al. |
| 2012/0135886 A1 | 5/2012 | Ruddock et al. |
| 2012/0231963 A1 | 9/2012 | Huang et al. |

FOREIGN PATENT DOCUMENTS

| | | |
|---|---|---|
| EP | 1 477 803 | 11/2004 |
| GB | 2324866 | 11/1998 |

(Continued)

OTHER PUBLICATIONS

Ayyildiz, A. et al."Mesane Tümorlerinde nukleer matriks protein 22 (NMP22) 'Nin sistoskopik bulgular, tumorun evresi ve derecesi ile karsilastirilmasi" / "Nuclear Matrix Protein 22 (NMP22) in the Bladder Tumor Comparison with the Findings of Cystoscopy, Stage and Grade of the Tumor" Turk Uroloji Dergisi, 2003, 29(3):277-284, Abstract.

(Continued)

*Primary Examiner* — Eric S DeJong
(74) *Attorney, Agent, or Firm* — Saliwanchik, Lloyd & Eisenschenk

(57) ABSTRACT

The invention provides a method of defining the likelihood of a subject having bladder cancer, comprising the steps of:
(A) assessing the subject's likelihood of having bladder cancer by: i. identifying at least one sub-population group appropriate to the subject; ii. determining the level of one or more biomarkers selected according to the sub-population group in a sample obtained from the subject; iii. inputting each of the biomarker values into an algorithm to produce an output value; and iv. correlating the output value with the likelihood of the subject having bladder cancer,
wherein the sub-population group is selected according to smoking habits, gender, presence/absence of stone disease, history of benign prostate enlargement (BPE) or prescription of anti-hypertensive, anti-platelet and/or anti-ulcer medication, and
(B) determining the subject's stratified risk level of serious disease by: v. determining the level of one or more biomarkers specific for one or more risk classifiers defined using Random Forest Classifiers (RFC), logistic regression or another appropriate systems biology or statistical approach in a sample obtained from the subject, vi. inputting each of the biomarker values into an algorithm or algorithms to produce an output value; and vii. correlating the output value with a stratified risk level of underlying serious disease,
wherein the likelihood of having bladder cancer is combined with the stratified risk level of having serious disease, wherein the risk of having bladder cancer and/or serious disease is categorized as: high-risk bladder cancer requiring immediate cystoscopy; low-risk bladder cancer requiring urgent cystoscopy; high-risk control requiring close evaluation and further investigation; or low-risk control requiring primary care monitoring.

18 Claims, 3 Drawing Sheets

(51) Int. Cl.
| | |
|---|---|
| G01N 33/574 | (2006.01) |
| G06F 19/24 | (2011.01) |
| G06F 19/00 | (2011.01) |
| G06G 7/58 | (2006.01) |

(52) U.S. Cl.
CPC . *G01N 2333/5421* (2013.01); *G01N 2333/55* (2013.01); *G01N 2333/70578* (2013.01); *G01N 2333/70596* (2013.01); *G01N 2333/7151* (2013.01); *G01N 2333/7452* (2013.01); *G01N 2333/928* (2013.01); *G01N 2333/96433* (2013.01); *G01N 2333/96494* (2013.01); *G01N 2333/988* (2013.01); *G01N 2400/00* (2013.01)

(56) References Cited

FOREIGN PATENT DOCUMENTS

| WO | WO-2005-043165 | 5/2005 |
|---|---|---|
| WO | WO-2009/017475 | 2/2009 |
| WO | WO-2011/012901 | 2/2011 |

OTHER PUBLICATIONS

Saied, G. et al. "Urine carcinoembryonic antigen levels are more useful than serum levels for early detection of Bilharzial and non-Bilharzial urinary bladder carcinoma: Observations of 43 Egyptian cases" World Journal of Surgical Oncology,2007, 5(4):1-6.

Abogunrin, F. et al., "The Impact of Biomarkers in Multivariate Algorithms for Bladder Cancer Diagnosis in Patients with Hematuria," Cancer, May 15, 2012, vol. 118, No. 10, pp. 2641-2650.

Emmert-Streib, F. et al., "Collectives of diagnostic biomarkers identify high-risk subpopulations of hematuria patients: exploiting heterogeneity in large-scale biomarker data," *BMC Medicine*, Jan. 17, 2013, vol. 11, pp. 1-15.

Alvarez, A. and Lokeshwar, B. "Bladder cancer biomarkers: current developments and future implementation" *Curr. Opin. Urol.*, 2007, vol. 17, pp. 341-346.

Chen, L. and Li, X. "Advancements in Bladder Cancer Markers" Journal of Clinical Oncology, 2008, vol. 35, No. 8, pp. 470-473.

Egawa, S. and Kuruma, H. "Search for Biomarkers of Aggressiveness in Bladder Cancer" *European Urology*, 2006, vol. 50, No. 1, pp. 20-22.

Helal, I. et al. "Comparison of C-Reactive Protein and High-Sensitivity C-Reactive Protein Levels in Patients on Hemodialysis" *Saudi Journal of Kidney Diseases and Transplantation*, 2012, vol. 23, No. 3, pp. 477-483.

Huben, R. "Tumor Markers in Bladder Cancer" *Supplement to Urology*, 1984, vol. 23, No. 3, pp. 10- 14.

Odisho, A. et al. "Reflex ImmunoCyt Testing for the Dialysis of Bladder Cancer in Patients with Atypical Urine Cytology" *European Urology*, 2013, vol. 63, pp. 936-940.

Rodgers, M. et al. "Diagnostic tests used in the investigation of adult haematuria: a systematic review" *Journal Compilation*, 2006, vol. 98, pp. 1154-1160.

Tetu, B. "Diagnosis of urothelial carcinoma from urine" *Modern Pathology*, 2009, vol. 22, No. S2, pp. S53-S59.

Voorzanger-Rousselot, N. and Garnero, P. "Biochemical Markers in Oncology. Part I: Molecular Basis. Part II: Clinical Uses" *Cancer Treatment Reviews*, 2007, Vol, 33, No. 3, pp. 230-283.

Williamson, K. et al. "Algorithmic Classifiers to Diagnose Bladder Cancer" *European Journal of Cancer*, Supplement, 2009, vol. 7, No. 3, p. 21, Abstract 48LBA.

Zweig, M. and Campbell, G. "Receiver-Operating Characteristic (ROC) Plots: A Fundamental Evaluation Tool in Clinical Medicine" *Clin. Chem.*, 1993, vol. 39, No. 4, pp. 561-577.

DIAGNOSIS AND RISK STRATIFICATION OF BLADDER CANCER

CROSS-REFERENCE TO RELATED APPLICATION

This application is the National Stage of International Application No. PCT/GB2013/052705, filed Oct. 16, 2013, which is hereby incorporated by reference herein in its entirety, including any figures, tables, nucleic acid sequences, amino acid sequences, or drawings.

FIELD OF INVENTION

The present invention relates to methods and biochips for stratifying the risk of developing bladder cancer.

BACKGROUND OF THE INVENTION

Bladder cancer is a leading cause of death worldwide. Most of the patients who present with superficial bladder cancer tumours will experience a recurrence within 5 years and almost 90% of these patients will have a recurrence within 15 years.

Haematuria, which refers to the presence of blood in urine, is a presenting symptom for a variety of diseases, including bladder cancer. The number of patients presenting with haematuria is progressively increasing in our aging population and the diagnosis of serious diseases in some of these patients can be delayed when triage is ineffective[1]. Therefore new risk stratification approaches are needed.

The final diagnosis for haematuria patients ranges from no diagnosis, through benign conditions including urinary infection, stone disease, benign prostate enlargement (BPE) to renal diseases and malignant causes. Urothelial cancer (UC), also known as transitional cell carcinoma (TCC), is the most common malignancy in haematuric patients and is the fourth most common cancer in men. UC was the estimated cause of death in 150,200 people, worldwide in 2008[3].

Bladder cancer is associated with many risk factors, for example its development is three times more common in men than in women[2]. However, this gender disparity is largely historical and is related to smoking habits. Smoking increases the risk of UC four-fold and cessation of smoking is associated with a decreased risk. Although UC is associated with smoking and carcinogen exposure, bladder cancers that arise following chronic inflammation are usually squamous cell carcinomas[2].

At the time of diagnosis, approximately 70% of patients diagnosed with UC have tumours that are pathologically staged as pTa, pT1 or carcinoma in situ (CIS) i.e., non-muscle invasive (NMI) disease and these patients can have a good prognosis. When a patient's tumour is pathologically defined as ≥T1G3 UC, the patient is deemed to have a high risk of progression to a more life threatening disease[2, 4]. Muscle invasive UC (MI UC) encompasses all pathological stages pT2. The risk parameters that are currently used to tailor follow-up for patients diagnosed with UC, include pathological parameters i.e., grade, stage and associated CIS, together with resistance to Bacille Calmette-Guerin treatment. However, it is not always possible to correctly predict the outcome for patients. This is largely attributable to the molecular heterogeneity within tumours which means that a spectrum of outcomes, spanning from negligible risk to life threatening prognosis, exists within the same pathologically classified groups. For this reason, all patients with NMI disease have frequent surveillance cystoscopies and those with MI have radiological surveillance for lymph node recurrence or distant metastasis[2].

Cystoscopy is the gold standard for the detection and surveillance of NMI UC[2]. However, this procedure is costly for health services and invasive for the patient. Furthermore, it requires a significant clinical input and has its own shortcomings[2, 5].

Cytology, another diagnostic test for bladder cancer, detects the presence of malignant cells in urine. Although cytology has high specificity, it has insufficient sensitivity to stand alone as a diagnostic test for UC in patients presenting with haematuria[2].

Despite their approval by the Food and Drug Administration (FDA), three diagnostic bladder cancer biomarkers, Nuclear Matrix Protein 22[6], Bladder Tumour Antigen (BTA)[7] and Fibrinogen Degradation Product[8], are not in use in routine practise as diagnostic biomarkers for UC because of their limited specificity. There is therefore a strong clinical need for urine-based tests which can at least risk stratify, and if possible, be diagnostic in haematuric patients[2].

Researchers often combine multiple tests, genes or biomarkers[9-11]. However, it is not possible to intuitively predict how multiple measurements, will collectively reflect the underlying biological heterogeneity in complex diseases, such as UC. Complex diseases consist of multiple components which interact to produce emergent properties that the individual components do not possess.

Therefore, there is a need for new approaches to identifying patients who are at risk of serious disease. It would be beneficial to enable clinicians to interpret risk classifiers alongside other clinical information at the time of triage, in order to reduce the number of cystoscopies and enable priority diagnosis of aggressive UC and other serious diseases, resulting in improved patient outcomes at reduced costs.

SUMMARY OF THE INVENTION

According to a first aspect, the present invention provides a method of defining the likelihood of a subject having bladder cancer, comprising the steps of:
(A) assessing the subject's likelihood of having bladder cancer by
  i. identifying at least one sub-population group appropriate to the subject;
  ii. determining the level of one or more biomarkers selected according to the sub-population group in a sample obtained from the subject;
  iii. inputting each of the biomarker values into an algorithm to produce an output value; and
  iv. correlating the output value with the likelihood of the subject having developing bladder cancer,
wherein the sub-population group is selected according to smoking habits, gender, presence/absence of stone disease, history of benign prostate enlargement (BPE) or prescription of anti-hypertensive, anti-platelet and/or anti-ulcer medication, and
(B) determining the subject's stratified risk level of having serious disease by
  v. determining the level of one or more biomarkers specific for one or more risk classifiers defined using Random Forest Classifiers (RFC), logistic regression or another appropriate systems biology or statistical approach in a sample obtained from the subject, vi. inputting each of the biomarker values into an algorithm or algorithms to produce an output value; and
vii. correlating the output value with a stratified risk level of underlying serious disease, wherein the likelihood of having bladder cancer is combined with the stratified risk level of having serious disease, and therefore each subject can be categorised as: high-risk bladder cancer requiring immediate cystoscopy; low-risk bladder cancer requiring urgent cystoscopy; high-risk control requiring close evaluation and further investigation; or low-risk control requiring primary care monitoring.

According to a second aspect, the invention provides a method of defining the likelihood of a subject having bladder cancer, comprising determining the level of a combination of biomarkers in a sample obtained from the subject, inputting each of the biomarker values into an algorithm to produce an output value and correlating the output value with the likelihood of the subject having bladder cancer, wherein if the subject is a smoker, the level of the biomarkers CRP, EGF, MMP9, IL-1α, IL-4, TM and IL-2 is determined;

if the subject is a non-smoker, the level of the biomarkers TNFα, sTNFR1, IL-6, IL-1α, MMP9/NGAL complex and CEA is determined and the creatinine level in the sample is also determined;

if the subject is male, the level of the biomarkers CRP, EGF, CK18, IL-1β, IL-8 and IL-2 is determined and the creatinine level in the sample is also determined;

if the subject is female, the level of the biomarkers CRP, EGF, IL-6, dDimer, MMP9/NGAL complex and CEA is determined and the osmolarity of the sample is also determined;

if the subject is positive for stone disease, the level of the biomarkers CRP, sTNFR1, CK18, IL-1α, IL-8 and VEGF is determined and the creatinine level in the sample is also determined;

if subject is negative for stone disease, the level of the biomarkers CRP, EGF, IL-6, IL-1α, MMP9/NGAL complex and CEA is determined and the creatinine level in the sample is also determined;

if the subject is positive for BPE, the level of the biomarkers CRP, EGF, IL-6, IL-1α, MMP9/NGAL complex, TM and CEA is determined;

if the subject is negative for PBE, the level of the biomarkers CRP, EGF, CK18, NGAL, MMP9/NGAL complex and BTA is determined and the creatinine level in the sample is also determined;

if the subject is positive for anti-hypertensive medication, the level of the biomarkers TNFα, EGF, IL-6, MMP9/NGAL complex and CEA is determined in and the creatinine level and total protein level in the sample is also determined;

if the subject is negative for anti-hypertensive medication, the level of the biomarkers TNFα, sTNFR1, IL-6, NGAL, IL-8, TM and CEA is determined;

if the subject is positive for anti-platelet medication, the level of the biomarkers TNFα, EGF, IL-6, IL-8 and CEA is determined and the total protein level and osmolarity of the sample is also determined;

if the subject is negative for anti-platelet medication, the level of the biomarkers CRP, EGF, MCP-1, MMP9/NGAL complex, TM and FPSA is determined and the total protein level of the sample is also determined;

if the subject is positive for anti-ulcer medication, the level of the biomarkers CRP, EGF, IL-6, IL-1α, IL-8, TM and CEA is determined; and if the subject is negative for anti-ulcer medication, the level of the biomarkers CRP, EGF, vWF, IL-1β, MMP9/NGAL complex, TM and HA is determined.

According to a third aspect, the present invention provides a solid state device comprising a substrate comprising an antibody to one or more of the biomarkers selected from CRP; EGF; IL-6; IL-1α; IL-4; TM; IL-2; TNFα; sTNFR1, STNFR2; MMP9; MMP9/NGAL complex; CEA; CK18; IL-1β; IL-8; dDimer; VEGF; NGAL; BTA; FPSA; NMP22; TPSA; vWF; HA; NSE; MCP1; FAS; and TUP.

According to further aspects of the invention, a solid state device according to the second aspect can be used to define the likelihood of a subject having bladder cancer or to stratify the risk of a subject having a serious underlying pathology, wherein combination of antibodies present on the solid state device are selected according to a sub-population group or natural cluster that is appropriate to the subject. The sub-population group is selected according to smoking habits, gender, presence/absence of stone disease, presence/absence of benign prostate enlargement (BPE) or history of prescribed anti-hypertensive, anti-platelet and/or anti-ulcer medication.

DESCRIPTION OF THE INVENTION

Figure 1:
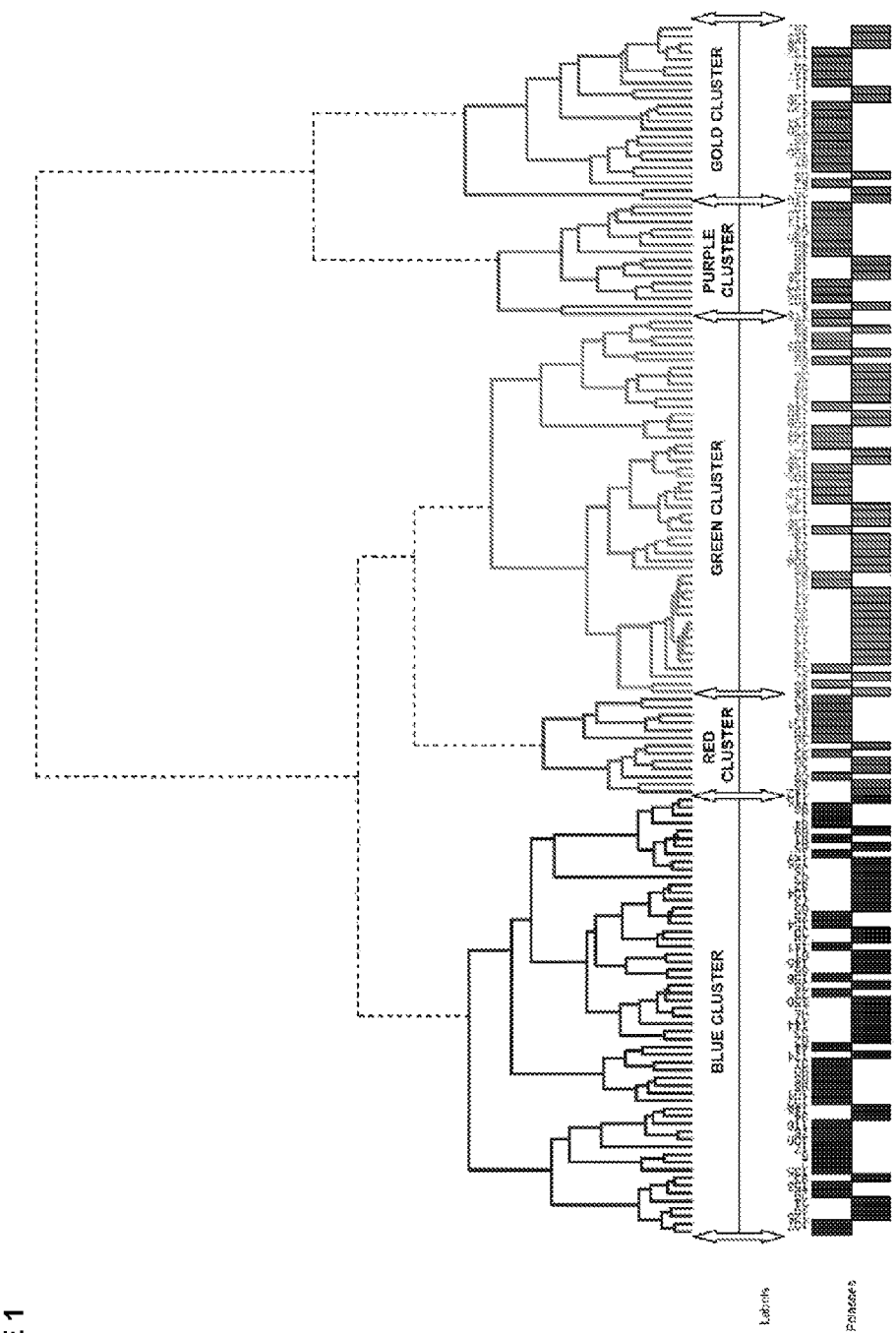
FIG. 1 shows hierarchical clustering of the 157 patients based on individual patient biomarker profiles.

The present invention provides both a method of defining the likelihood of a subject having bladder cancer and a method of stratifying the risk of a subject having a serious underlying disease state. The method is advantageous as it provides clinicians with two risk assessments which in combination are more powerful and can be used, preferably alongside other clinical information, at the time of triage. Using the method of the invention, each patient can be assigned a likelihood of having bladder cancer and a likelihood of having serious disease. As a result, the number of invasive cystoscopy procedures can be reduced. Furthermore, the invention enables priority diagnosis of aggressive bladder cancer and other serious diseases, leading to improved patient outcomes at reduced costs.

The method of the invention involves two steps: a first 'diagnostic' step and a second 'risk stratification' step.

The first diagnostic step involves defining the subject's likelihood of having bladder cancer by:
  i. identifying at least one clinical sub-population group appropriate to the subject;
  ii. determining the level of one or more biomarkers selected according to the sub-population group in a sample obtained from the subject;
  iii. inputting each of the biomarker values into an algorithm to produce an output value; and
  iv. correlating the output value with risk of having bladder cancer, wherein the clinical sub-population group is selected according to smoking habits, gender, presence/absence of stone disease, history of BPE or prescription of anti-hypertensive, anti-platelet and/or anti-ulcer medication.

The second risk stratification step involves determining the subject's stratified risk level of having a serious disease by v. determining the level of one or more biomarkers specific for one or more risk classifiers defined using Random Forest Classifiers (RFC), logistic regression or another appropriate systems biology or statistical approach in a sample obtained from the subject, vi. inputting each of the biomarker values into an algorithm or algorithms to produce an output value;

vii. correlating the output value with a stratified risk level of serious disease.

The likelihood of having bladder cancer is combined with the likelihood of having serious disease, and therefore each subject can be categorised as: high-risk bladder cancer requiring immediate cystoscopy; low-risk bladder cancer requiring urgent cystoscopy; high-risk control requiring close evaluation and further investigation; or low-risk control requiring primary care monitoring.

In the context of the present invention the term "bladder cancer" is understood to include urothelial carcinoma (UC), transitional cell carcinoma, bladder squamous cell carcinoma and/or bladder adenocarcinoma. Preferably, the bladder cancer is urothelial carcinoma.

The terms "subject" and "patient" are used interchangeably herein and refer to a mammal including a non-primate (e.g. a cow, pig, horse, dog, cat, rat and mouse) and a primate (e.g. a monkey and human). Preferably the subject or patient is a human.

Preferably, the subject is a patient a presenting with haematuria. For the avoidance of doubt, the term "haematuria" refers to the presence of red blood cells in the urine. Haematuria may be caused by a number of conditions, such as bladder cancer, BPE, kidney stones and infection, prostate cancer, renal cell carcinoma or urinary tract infections.

Preferably, the biomarkers are detected in at least one sample obtained from the subject, selected from a urine sample, whole blood sample, serum sample or plasma sample.

The terms "serious disease" and "serious underlying pathology" are used interchangeably herein, and refer to life-threatening conditions such as kidney disease, aggressive bladder cancer or other aggressive cancers.

The term "smoking habits" refers herein to whether or not the subject smokes. The term "smoking" includes all forms of tobacco smoking, including cigarettes, cigars and pipe tobacco. An individual subject is either classified as positive (i.e. is a smoker) or negative (i.e. is not a smoker) for smoking habits.

The term "gender" refers to whether the subject is male or female.

The phrase "presence/absence of renal stone disease" refers herein to whether or not the subject has a history of renal stones or inflammation of the bladder or urinary tract. An individual subject is either classified as positive (i.e. has a history of renal stones/inflammation) or negative (i.e. no history of renal stones/inflammation). "Renal stones" is also referred to herein as "stone disease".

The phrase "history of benign prostate enlargement (BPE)" refers herein to whether or not the subject has a history of BPE. For the avoidance of doubt, BPE is an increase in the size of prostate. An individual subject is either classified as positive (i.e. has a history of, BPE) or negative (i.e. no history of BPE).

As used herein, the phrases "prescription of anti-hypertensive", "prescription of anti-platelet medication" and "prescription of anti-ulcer medication" refer to whether or not the subject is prescribed one or more of these medications. For the purpose of the method of the invention, each medication is considered separately. Therefore an individual subject could be positive for one or more medications but negative for one or more of the other two.

For the avoidance of doubt, anti-hypertensives are a class of drugs used to treat hypertension (high blood pressure). The most widely used include thiazide diuretics, angiotensin-converting-enzyme (ACE) inhibitors, calcium channel blockers, beta-blockers, and angiotensin II receptor antagonists or angiotensin-receptor blockers (ARBs). Anti-platelet medications are a class of drugs that decrease platelet aggregation and inhibit thrombus formation. This class of drugs includes irreversible cyclooxygenase inhibitors, adenosine diphosphate (ADP) receptor inhibitors, phosphodiesterase inhibitors, glycoprotein IIB/IIIA inhibitors and adenosine re-uptake inhibitors. Anti-ulcer medications are a class of drugs used to treat ulcers in the stomach and the upper part of the small intestine. The most widely used include proton pump inhibitors (such as omeprazole, lansoprazole, pantoprazole and rabeprazole), H-2 receptor blocking agents (such as cimetidine, famotidine, nizatidine, and ranitidine) and sucralfate.

The word "history" is sometimes abbreviated herein to "Hx".

The biomarkers are selected from the list comprising: CRP; EGF; IL-6; IL-1α, MMP9; IL-4; TM; IL-2; TNFα; sTNFR1, sTNFR2, MMP9/NGAL complex; CEA; CK18, IL-1β; IL-8; dDimer; VEGF; NGAL; BTA; FPSA; TPSA; NMP22; vWF; HA; NSE; MCP1, FAS; and TUP.

Preferably, CRP; EGF; IL-6; IL-1α; MMP9; IL-4; TM; IL-2; TNFα; sTNFR1, sTNFR2, MMP9/NGAL complex; CK18, IL-1β; IL-8; dDimer; VEGF; NGAL; BTA; vWF; HA; NSE; MCP1, NMP22; and FAS are measured in a urine sample and TPSA, FPSA and CEA are measured in a serum sample.

Osmolarity, total urinary protein (TUP) and/or creatinine levels in the sample may also be measured and the resulting value(s) included in the statistical analysis. Creatinine is a product of creatine phosphate metabolism in muscle tissue. Creatinine levels (µmol/L) can be measured using a Daytona RX Series Clinical Analyser (Randox). Osmolarity, or osmotic concentration, is the measure of solute concentration, defined as the number of osmoles (Osm) of solute per liter of solution (Osm/L). Osmolarity can be measured using a Löser Micro-Osmometer (Type 15) (Löser Messtechnik, Germany). TUP levels (mg/ml) can be measured in a urine sample by Bradford assay $A_{595}$ nm (Hitachi U2800 spectrophotometer) using bovine serum albumin as the standard. The skilled person will be familiar with each of these techniques.

If the smoker sub-population is selected in step A(i), the level of the biomarkers CRP, EGF, MMP9, IL-1α, IL-4, TM and IL-2 is determined in step A(ii).

If the non-smoker sub-population is selected in step A(i), the level of the biomarkers TNFα, sTNFR1, IL-6, IL-1α, MMP9/NGAL complex and CEA is determined in step A(ii) and the creatinine level in the sample is also determined.

If the gender sub-population is selected in step A(i), and the subject is male, the level of the biomarkers CRP, EGF, CK18, IL-1β, IL-8 and IL-2 is determined in step A(ii) and the creatinine level in the sample is also determined.

If the gender sub-population is selected in step A(i), and the subject is female, the level of the biomarkers CRP, EGF, IL-6, dDimer, MMP9/NGAL complex and CEA is determined in step A(ii) and the osmolarity of the sample is also determined.

If the stone disease sub-population is selected in step A(i), and the subject is positive for stone disease, the level of the biomarkers CRP, sTNFR1, CK18, IL-1α, IL-8 and VEGF is determined in step A(ii) and the creatinine level in the sample is also determined.

If the stone disease sub-population is selected in step A(i), and the subject is negative for stone disease, the level of the biomarkers CRP, EGF, IL-6, IL-1α, MMP9/NGAL complex and CEA is determined in step A(ii) and the creatinine level in the sample is also determined.

If the BPE sub-population is selected in step A(i), and the subject is positive for BPE, the level of the biomarkers CRP, EGF, IL-6, IL-1α, MMP9/NGAL complex, TM and CEA is determined in step A(ii).

If the BPE sub-population is selected in step A(i), and the subject is negative for PBE, the level of the biomarkers CRP, EGF, CK18, NGAL, MMP9/NGAL complex and BTA is determined in step A(ii) and the creatinine level in the sample is also determined.

If the anti-hypertensive medication sub-population is selected in step A(i), and the subject is positive for anti-hypertensive medication, the level of the biomarkers TNFα, EGF, IL-6, MMP9/NGAL complex and CEA is determined in step A(ii) and the creatinine level and TUP level in the sample is also determined.

If the anti-hypertensive medication sub-population is selected in step A(i), and the subject is negative for anti-hypertensive medication, the level of the biomarkers TNFα, sTNFR1, IL-6, NGAL, IL-8, TM and CEA is determined in step A(ii).

If the anti-platelet medication sub-population is selected and the subject is positive for anti-platelet medication, the level of the biomarkers TNFα, EGF, IL-6, IL-8 and CEA is determined in step (ii) and the TUP level and osmolarity of the sample is also determined.

If the anti-platelet medication sub-population is selected in step A(i), and the subject is negative for anti-platelet medication, the level of the biomarkers CRP, EGF, MCP-1, MMP9/NGAL complex, TM and FPSA is determined in step A(ii) and the TUP level of the sample is also determined.

If the anti-ulcer medication sub-population is selected in step A(i), and the subject is positive for anti-ulcer medication, the level of the biomarkers CRP, EGF, IL-6, IL-1α, IL-8, TM and CEA is determined in step A(ii).

If the anti-ulcer medication sub-population is selected in step A(i), and the subject is negative for anti-ulcer medication, the level of the biomarkers CRP, EGF, vWF, IL-1β, MMP9/NGAL complex, TM and HA is determined in step A (ii).

The "level" of a combination of biomarkers refers to the amount or concentration in each biomarker of the combination of biomarkers within the sample.

The term "natural clusters" refers to groups of biomarkers identified herein by different colours (see Tables 3 and 4). Blue and green clusters have been found to be associated with low risk of serious disease, whereas the red, purple and gold clusters have been found to be associated with high risk of serious disease. The patient clusters have been defined following agglomerative clustering, as illustrated in FIG. 1.

Steps (iii) and (vi) of the method of the invention are carried out by inputting biomarker values into an algorithm or algorithms to produce an output value. The accuracy of the methods which are the subject of the invention is best described by their receiver-operating characteristics (ROC).

The ROC graph is a plot of all of the sensitivity/specificity pairs resulting from continuously varying the decision threshold over the entire range of data observed. To construct a ROC curve for multiple biomarkers, a logistic regression equation is derived for the biomarker combination of interest, by inputting measured protein concentration value of each of the biomarkers in a patient's sample into the equation.

Although a logistic regression equation is the preferred statistical method for the current invention, other conventional statistical methods can be used.

The combinations of biomarkers used to diagnose bladder cancer in the present invention have a sensitivity and specificity of at least 70%. This means that out of 100 patients which have bladder cancer, 70% of them will be correctly identified from the determination of the presence of a particular combination of biomarkers as positive for bladder cancer while out of 100 patients who do not have bladder cancer 70% will accurately test negative for the disease.

A ROC plot depicts the overlap between the two distributions by plotting the sensitivity versus 1−specificity for the complete range of decision thresholds. On the y-axis is sensitivity, or the true-positive fraction defined as [(number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always 0.5. Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive the level of how close the ROC plot is to the perfect one (area=1.0).

Scores between 0 and 1 make it possible to assign a subject as a "low-risk control" (i.e. requiring primary care monitoring), a "high-risk control" (i.e. requiring close evaluation and further investigation), a "low-risk bladder cancer" (i.e. requiring urgent cystoscopy) or a "high-risk bladder cancer" (i.e. requiring immediate cystoscopy). Scores <0.4 indicate that the risk of serious disease is low, or if the initial diagnostic step has also been carried out and produces a score <0.4, it is unlikely that the subject has UC. A score >0.6 indicates a high risk of serious disease, or that the patient could have UC if the score is based on the initial diagnostic step. Scores between 0.4 and 0.6 can be interpreted as indicative of potential risk and the possibility of UC. Subjects with scores of 0.2 from the method of the invention (and the initial diagnostic step if that is carried out) and no clinical risk factors are identified as low-risk controls. Such subjects could be monitored in primary care.

Part (B) of the method of the invention comprises the step of determining the level of one or more biomarkers specific for one or more risk classifiers defined using Random Forest Classifiers (RFC), logistic regression or another appropriate systems biology or statistical approach in a sample obtained from the subject. RFC is an ensemble method consisting of multiple decision trees which, taken together, can be used to assign each subject into either of two categories on the basis of individual biomarker profiles. As the skilled person will understand, the term "logistical regression" refers to a type of regression analysis used for predicting the outcome of a categorical criterion variable (a variable that can take on a limited number of categories) based on one or more predictor variables. The probabilities describing the possible outcome of a single trial are modeled as a function of explanatory variables using a logistic function. Logistic regression measures the relationship between a categorical dependent variable and usually a continuous independent variable (or several), by converting the dependent variable to probability scores.

The methods of the invention are carried out using a substrate having at least one antibody against each of the biomarkers included in the at least one combination of biomarkers.

The antibodies used in the present invention can be of any conventional type. Polyclonal and monoclonal antibodies are preferred, with monoclonal antibodies being most preferred. As used herein, the term "antibody" includes any immunoglobulin or immunoglobulin-like molecule or fragment thereof, Fab fragments, ScFv fragments and other antigen binding fragments. The term "monoclonal antibodies" refers to a homogeneous population of antibodies (including antibody fragments), which recognise a single epitope on a target.

The method of the invention may be carried out two or more times for each individual subject by selecting two or more sub-population groups appropriate to the subject and determining the level of one or more biomarkers selected according to the sub-population groups.

Furthermore, the method may optionally comprise an additional diagnostic step of determining whether the subject is high or low-risk of bladder cancer. This additional step comprises determining the level of one or more bladder cancer markers selected from BTA, CEA, TM, NMP22, EGF, TNFα, NSE, NGAL, MMP9/NGAL complex, FAS, IL-6, IL-1α, CRP, sTNFR1, sTFR2 vWF, IL-1β, HA, CK18, VEGF, IL-8, IL-2, d-Dimer, MMP-9, IL-4, TUP, FPSA and TPSA. The diagnostic step may be carried out before, after or at the same time as carrying out the method of the invention to stratify the subject's risk of serious disease.

In one embodiment, the additional diagnostic step is carried out by assaying A sample from the subject for the levels of at least one combination of biomarkers selected from the combination of i) BTA, CEA and TM, and the combination of ii) NMP22 and EGF, wherein the levels of the at least one combination of biomarkers is assayed by contacting the sample with a substrate having at least one antibody against each of the biomarkers included in the at least one combination of biomarkers; providing the results of the assay for the levels of the at least one combination of biomarkers; wherein an increase in levels of the biomarkers in combination i) or an increase in the level of NMP22 and a decrease in the level of EGF in combination ii) compared to a control value indicates bladder cancer in the subject. This is described in Abogunrin et al., "The impact of biomarkers in multivariate algorithms for bladder cancer diagnosis in patients with hematuria" Cancer (2012) 118 (10):2641-50.

In addition to the above embodiment, the determination of whether the subject is at high or low-risk of bladder cancer may also or instead involve detecting the presence of at least two biomarkers selected from CEA, VEGF, IL-8, NGAL, NSE, IL-2, EGF, TM, d-Dimer, MMP-9, IL-6, IL-4, MMP-9/NGAL complex, FAS, CRP, TUP and NMP22 in one or more samples isolated from the subject, wherein the presence of a combination of at least two of the biomarkers in the one or more samples indicates the presence or risk of bladder cancer. These biomarker of bladder cancer are known in the art, see for example WO2010/012901.

Preferably, the additional diagnostic step comprises determining the level of one or more biomarkers in a sample obtained from the subject selected from the groups (1) TNFα, EGF, NSE, NGAL, MMP9/NGAL, TM and FAS; (2) TNFα, EGF, IL-6, IL-1α, MMP9/NGAL, TM and CEA; or (3) CRP, sTNFR1, vWF, IL-1β, MMP9/NGAL and BTA, according to the sub-population group in a sample obtained from the subject; inputting each of the biomarker values into a ROC statistical analysis to obtain a AUROC value; and correlating the AUROC value with a high or low risk of developing bladder cancer, wherein if the biomarkers of group (3) are selected, creatinine levels in the sample are also measured and the value(s) included in the ROC statistical analysis.

In the context of the above additional diagnostic steps, a "control" or "control value" is understood to mean the level of a particular biomarker typically found in patients who do not have bladder cancer. The control level of a biomarker may be determined by analysis of a sample isolated from a person with haematuria but who does not have bladder cancer or may be the level of the biomarker understood by the skilled person to be typical for such a person. The control value of a biomarker may be determined by methods known in the art and normal values for a biomarker may be referenced from the literature from the manufacturer of an assay used to determine the biomarker level.

A number of biomarkers present in a sample isolated from a patient having bladder cancer may have levels which are different to that of a control. However, the levels of some of the biomarkers that are different compared to a control may not show a strong enough correlation with bladder cancer such that they may be used to diagnose bladder cancer with an acceptable accuracy.

The invention may further comprise administering therapy to the subject, based on their risk of having bladder cancer and/or serious disease as determined by the method of the invention. Appropriate therapy may include administering known therapeutic agents to treat or prevent bladder cancer.

In a separate aspect, the invention provides a method of defining the likelihood of a subject having bladder cancer, comprising determining the level of a combination of biomarkers in a sample obtained from the subject, inputting each of the biomarker values into an algorithm to produce an output value and correlating the output value with the likelihood of the subject having bladder cancer, wherein:

if the subject is a smoker, the level of the biomarkers CRP, EGF, MMP9, IL-1α, IL-4, TM and IL-2 is determined;

if the subject is a non-smoker, the level of the biomarkers TNFα, sTNFR1, IL-6, IL-1α, MMP9/NGAL complex and CEA is determined and the creatinine level in the sample is also determined;

if the subject is male, the level of the biomarkers CRP, EGF, CK18, IL-1β, IL-8 and IL-2 is determined and the creatinine level in the sample is also determined; if the subject is female, the level of the biomarkers CRP, EGF, IL-6, dDimer, MMP9/NGAL complex and CEA is determined and the osmolarity of the sample is also determined;

if the subject is positive for stone disease, the level of the biomarkers CRP, sTNFR1, CK18, IL-1α, IL-8 and VEGF is determined and the creatinine level in the sample is also determined;

if subject is negative for stone disease, the level of the biomarkers CRP, EGF, IL-6, IL-1α, MMP9/NGAL complex and CEA is determined and the creatinine level in the sample is also determined;

if the subject is positive for BPE, the level of the biomarkers CRP, EGF, IL-6, IL-1α, MMP9/NGAL complex, TM and CEA is determined;

if the subject is negative for PBE, the level of the biomarkers CRP, EGF, CK18, NGAL, MMP9/NGAL complex and BTA is determined and the creatinine level in the sample is also determined;

if the subject is positive for anti-hypertensive medication, the level of the biomarkers TNFα, EGF, IL-6, MMP9/NGAL complex and CEA is determined in and the creatinine level and total protein level in the sample is also determined;

if the subject is negative for anti-hypertensive medication, the level of the biomarkers TNFα, sTNFR1, IL-6, NGAL, IL-8, TM and CEA is determined;

if the subject is positive for anti-platelet medication, the level of the biomarkers TNFα, EGF, IL-6, IL-8 and CEA is determined and the total protein level and osmolarity of the sample is also determined;

if the subject is negative for anti-platelet medication, the level of the biomarkers CRP, EGF, MCP-1, MMP9/NGAL complex, TM and FPSA is determined and the total protein level of the sample is also determined;

if the subject is positive for anti-ulcer medication, the level of the biomarkers CRP, EGF, IL-6, IL-1α, IL-8, TM and CEA is determined; and if the subject is negative for anti-ulcer medication, the level of the biomarkers CRP, EGF, vWF, IL-1β, MMP9/NGAL complex, TM and HA is determined. The algorithm used to produce the output value is preferably an algorithm as described above.

Another aspect of the present invention provides a solid state device comprising a substrate comprising an antibody to one or more of the biomarkers selected from CRP; EGF; IL-6; IL-1α; MMP9; NMP22; IL-4; TM; IL-2; TNFα; sTNFR1, STNFR2; MMP9/NGAL complex; CEA; CK18, IL-1β; IL-8; dDimer; VEGF; NGAL; BTA; FPSA; TPSA; vWF; HA; NSF; MCP1; FAS; and TUP.

The antibodies used in the present invention can be of any conventional type. Polyclonal and monoclonal antibodies are preferred, with monoclonal antibodies being most preferred.

A device that may be used in the invention may be prepared by activating the surface of a suitable substrate, and applying an array of antibodies on to discrete sites on the surface. If desired, the other active areas may be blocked. The ligands may be bound to the substrate via a linker. In particular, it is preferred that the activated surface is reacted successively with an organosilane, a bifunctional linker and the antibody. The solid state device used in the methods of the present invention may be manufactured according to the method disclosed in, for example, GB-A-2324866 the content of which is incorporated herein in its entirety. Preferably, the solid state device used in the methods of the present invention is the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

The solid state device may be used, either alone or in combination with other clinical indicators, to assess the risk of a subject having bladder cancer and/or stratify the level of risk of serious disease, wherein combination of antibodies present on the solid state device are selected according to a sub-population group that is appropriate to the subject.

At least one, but optionally two or more different solid state devices according to the invention may be used for each individual subject in order to assess their risk of having bladder cancer. If multiple devices are used, each will comprise a combination of antibodies selected according to sub-population groups that are appropriate to the subject.

A solid state device comprising antibodies to CRP, EGF, MMP9, IL-1α, IL-4 and TM and IL-2 can be used to assess the likelihood of bladder cancer in a subject who is a smoker.

A solid state device comprising antibodies to TNFα, sTNFR1, IL-6, IL-1α, MMP9/NGAL complex and CEA can be used to assess the likelihood of bladder cancer in a subject who is not a smoker.

A solid state device comprising antibodies to CRP, EGF, CK18, IL-1β, IL-8 and IL-2 can be used to assess the likelihood of bladder cancer in a male subject.

A solid state device comprising antibodies to CRP, EGF, IL-6, dDimer, MMP9/NGAL complex and CEA can be used to assess the likelihood of bladder cancer in a female subject.

A solid state device comprising antibodies to CRP, sTNFR1, CK18, IL-1α, IL-8 and VEGF can be used to assess the likelihood of bladder cancer in a subject who is positive for renal stone disease.

A solid state device comprising antibodies to CRP, EGF, IL-6, IL-1α, MMP9/NGAL complex and CEA can be used to assess the likelihood of bladder cancer in a subject who is negative for renal stone disease.

A solid state device comprising antibodies to CRP, EGF, IL-6, IL-1α, MMP9/NGAL complex, TM and CEA can be used to assess the likelihood of bladder cancer in a subject who is positive for BPE.

A solid state device comprising antibodies to CRP, EGF, CK18, NGAL, MMP9/NGAL complex and BTA can be used to assess the likelihood of bladder cancer in a subject who is negative for BPE.

A solid state device comprising antibodies to TNFα, EGF, IL-6, MMP9/NGAL complex and CEA can be used to assess the likelihood of bladder cancer in a subject who is positive for anti-hypertensive medication.

A solid state device comprising antibodies to TNFα, sTNFR1, IL-6, NGAL, IL-8, TM and CEA can be used to assess the likelihood of bladder cancer in a subject who is negative for anti-hypertensive medication.

A solid state device comprising antibodies to TNFα, EGF, IL-6, IL-8 and CEA can be used to assess the likelihood of bladder cancer in a subject who is positive for anti-platelet medication.

A solid state device comprising antibodies to CRP, EGF, MCP-1, MMP9/NGAL complex, TM and FPSA can be used to assess the likelihood of bladder cancer in a subject who is negative for anti-platelet medication.

A solid state device comprising antibodies to CRP, EGF, IL-6, IL-1α, IL-8, TM and CEA can be used to assess the likelihood of bladder cancer in a subject who is positive for anti-ulcer medication.

A solid state device comprising antibodies to CRP, EGF, vWF, IL-1β, MMP9/NGAL complex, TM and HA can be used to assess the likelihood of bladder cancer in a subject who is negative for anti-ulcer medication.

Solid state devices comprising antibodies to TNFα, EGF, NSE, NGAL, MMP9/NGAL, TM and FAS, or comprising antibodies to TNFα, EGF, IL-6, IL-1α, MMP9/NGAL, TM and CEA, or comprising antibodies to CRP, sTNFR1, vWF, IL-1α, MMP9/NGAL and BTA can be used to assess the likelihood of a subject having bladder cancer and/or stratify the level of risk of serious disease.

The invention is further described with reference to the following non-limiting examples:

Examples

The present inventors pursued a systems approach using clustering and Random Forests Classification (RFC) to analyse clinical and demographic information together with biomarker measurements which were available from each of 157 haematuric patients; 80 patients with UC and 77 controls. The inventors exploited the heterogeneity in this large scale biomarker dataset by allowing the patients to cluster naturally on the basis of their individual biomarker profiles. Clustering identified five patient clusters. Three of these patient clusters were enriched with patients with known cancer-risk characteristics. The remaining two patient clusters were enriched with patients with non-cancer characteristics.

Patient Information and Samples

The inventors analysed data collected during a case-control study approved by the Office for Research Ethics Committees Northern Ireland (ORECNI 80/04); and reviewed by hospital review boards. The study was conducted according to STARD guidelines[14, 15]. Written consent was obtained from patients with haematuria who had recently undergone cystoscopy or for whom cystoscopy was planned. Patients (n=181) were recruited between November 2006 and October 2008[9]. A single consultant pathologist undertook a pathological review of the diagnostic slides for all bladder cancer patients. Bladder cancer patients who were disease-free when sampled (n=19), had adenocarcinoma (n=1) or squamous cell carcinoma (n=1); and patients aged ≥85 years (n=3) were excluded from our analyses. The inventors therefore analysed data from 157 patients.

A single consultant cytopathologist reviewed the cytology from 74 bladder cancer and 65 control patients. There were insufficient cells for diagnosis in 18/157 patients. The final diagnosis for each of the 157 patients was determined individually. Diagnosis was based on history, physical examination, urinary tract radiological and endoscopy findings and the pathological reports relating to biopsy or re-section specimens. Each patient was assigned to one of seven final diagnosis categories: "no diagnosis", "benign pathologies", "stones/inflammation", "BPE", "other cancers", "NMI UC" or "MI UC". In 36/157 (23%) patients, it was not possible to identify the underlying cause for haematuria, even after detailed investigations, including cystoscopy and radiological imaging of the upper urinary tract. The diagnosis for these patients was "no diagnosis". For analyses purposes, the inventors grouped "no diagnosis", "benign pathologies", "stones/inflammation" and "BPE" together as non-life threatening diagnoses (NLT); and grouped "other cancers", "NMI UC" and "MI UC" together as life threatening diagnoses (LT). This information is presented in Table 1.

TABLE 1

| Individual patient final diagnosis | n | Final diagnosis category | Group | Total |
|---|---|---|---|---|
| No diagnosis | 36 | No diagnosis | NLT | 36 |
| Category total | | | | 36 |
| Fistula | 1 | Benign | NLT | |
| Endometriosis | 1 | Benign | NLT | |
| Trauma | 1 | Benign | NLT | |
| Renal trauma | 1 | Benign | NLT | |
| Renal cyst | 1 | Benign | NLT | |
| Squamus Metaplasia | 1 | Benign | NLT | |
| Category total | | | | 6 |
| Stone | 9 | Stones/inflammation | NLT | |
| Stone(s) with inflammation | 2 | Stones/inflammation | NLT | |
| Stone with UTI | 1 | Stones/inflammation | NLT | |
| Urinary tract infection | 1 | Stones/inflammation | NLT | |
| Inflammation | 4 | Stones/inflammation | NLT | |
| Category total | | | | 17 |
| BPE with stone | 2 | BPE | NLT | |
| BPE | 10 | BPE | NLT | |
| Category total | | | | 12 |
| Renal cell carcinoma with BPE | 1 | Other cancers | LT | |
| Renal cell carcinoma | 2 | Other cancers | LT | |
| Prostate cancer | 3 | Other cancers | LT | |
| Category total | | | | 6 |
| UC kidney ureter | 1 | NMI UC | LT | |
| NMI TCC with stone | 2 | NMI UC | LT | |
| NMI TCC with BPE | 1 | NMI UC | LT | |
| NMI TCC | 58 | NMI UC | LT | |
| Category total | | | | 62 |
| MI UC with stone | 2 | MI UC | LT | |
| MI UC with BPE | 2 | MI UC | LT | |
| MI UC | 14 | MI UC | LT | |
| Category total | | | | 18 |
| TOTAL | | | | 157 |

Biomarker Measurement

Biomarker measurements were undertaken on anonymised samples at Randox Laboratories Ltd. For each patient, we measured 23 biomarkers in triplicate and 3 in singlet. TUP, osmolarity and creatinine levels were also measured (see Table 2). Samples were stored at −80° C. for a maximum of 12 months (Table 2). Creatinine levels (μmol/L) and Osmolarity (mOsm) were measured using a Daytona RX Series Clinical Analyser (Randox) and a Löser Micro-Osmometer (Type 15) (Löser Messtechnik, Germany), respectively. TUP levels (mg/ml) in urine were determined by Bradford assay $A_{595}$ nm (Hitachi U2800 spectrophotometer) using bovine serum albumin as the standard. The inventors classified proteinuria as TUP >0.25 mg/ml[16]. Eighteen biomarkers in urine, and carcino-embryonic antigen (CEA) and free prostate specific antigen (FPSA) in serum, were measured using Randox Biochip Array Technology (Randox Evidence™ and Investigator™), which are multiplex systems for protein analysis[17]. An additional four biomarkers were measured using commercially available ELISAs. Epidermal growth factor (EGF) and the matrix metalloproteinase 9 neutrophil-associated gelatinase lipocalin (MMP9-NGAL) were measured using in-house ELISAs (see Table 2).

Data Representation

Data were represented by a matrix X with 157 rows and 29 columns e.g., X(3,5) contained the measurement for patient number 3 and biomarker number 5. Each component of X corresponds to the mean value of the triplicate measurements. In order to simplify the notation, we denoted by X(j,) the 29 dimensional feature vector for patient j and by X(,k) the 157 dimensional feature vector for biomarker k.

Identification of Patient Clusters

The inventors conducted a hierarchical clustering with a Canberra distance and a Mcquitty clustering[18] to assess the similarity between the profile vectors of all patients using, e.g., X(i,) as a profile vector for patient i. Patients were thus separated into clusters according to the similarities of their 29 biomarkers i.e., each patient's profile vector was based on the measured the levels of the 29 biomarkers in their urine or serum samples. This means that instead of using clinical information from the patients such as their medication or behavioural habits, we used only the patient biomarker data set to obtain the categorisation. To demonstrate the robustness of the observed clusters, we repeated the same analysis 100 times using only a bootstrap subset of the patients to conduct the clustering.

Chi-Square Tests

The inventors were interested to determine whether patients with specific final diagnoses or known cancer risk characteristics were randomly distributed across the patient clusters. The inventors matched clinical information to the patient clusters and then constructed five cross-tables placing the patient clusters in rows. The final diagnosis categories, absence/presence of proteinuria, pathological stages, pathological grades, or absence/presence of malignant cytology were listed in the columns. When the number of observed counts was <5 in >80% of cells in any of these tables, the inventors merged groups, as appropriate prior to undertaking Chi-square tests (see Table 1 above).

Identification of Biomarker Clusters

To allow the inventors to exploit the full complement of biomarker data for subsequent classification of patient clusters and patient subpopulations, they conducted hierarchical clustering to identify substructures within the 29 biomarkers themselves. For each biomarker k, they used X(,k) as a profile vector to conduct an agglomerative clustering for the 29 biomarkers. Therefore each biomarker's profile vector was based on the levels of the biomarker measured in each of the 157 patients. On the assumption that biomarkers in the

TABLE 2

| Biomarker | Units | Analysis | Clinical Application |
|---|---|---|---|
| Protein | mg/ml | Bradford assay | Kidney disease |
| Creatinine | μmol/L | Daytona RX Series Clinical Analyser (Randox) | Kidney disease |
| Osmolarity | mOsm | Löser Micro-Osmometer (Type 15) (Löser Messtechnik. Germany) | Kidney disease |
| Bladder tumour antigen (BAT) | U/ml | ELISA (Polymedco) | UC diagnosis |
| Carcino-embryonic antigen (CEA) | ng/ml | BAT | Monitoring colorectal cancer |
| Cytokeratin 18 (CK18) | ng/ml | ELISA (USCNLIFE Science & Technology Co. Ltd) | N/A |
| C-reactive protein (CRP) | ng/ml | BAT | Acute inflammation/infection |
| d-Dimer | ng/ml | BAT | Pulmonary embolus |
| Epidermal growth factor (EGF) | pg/ml | ELISA (in-house) | US prognosis |
| FAS | pg/ml | BAT | N/A |
| Hyaluronidase (HA) | ng/ml | BAT | N/A |
| Interleukin-1α (IL-1α) | pg/ml | BAT | N/A |
| Interleukin-1β (IL-1β) | pg/ml | BAT | N/A |
| Interleukin-2 (IL-2) | pg/ml | BAT | N/A |
| Interleukin-4 (IL-4) | pg/ml | BAT | N/A |
| Interleukin-6 (IL-6) | pg/ml | BAT | N/A |
| Interleukin-8 (IL-8) | pg/ml | BAT | N/A |
| Monocyte chemo-attractant protein-1 (MCP-1) | pg/ml | BAT | N/A |
| Matrix metalloproteinase 9 (MMP9) | ng/ml | BAT | N/A |
| MMP-9/NGAL complex | N/A | ELISA (in-house) | N/A |
| Neutrophil-associated gelatinase lipocalin (NGAL) | ng/ml | BAT | Kidney disease |
| Neuron-specific enolase (NSE) | ng/ml | BAT | N/A |
| Free prostate specific antigen (FPSA) | ng/ml | BAT | Prostate cancer |
| Thrombomodulin (TM) | ng/ml | BAT | N/A |
| Tumour necrosis factor α (TNFα) | pg/ml | BAT | N/A |
| Soluble tumour necrosis factor receptor 1 (sTNFR1) | ng/ml | BAT | N/A |
| Soluble tumour necrosis factor receptor 2 (sTNFR2) | ng/ml | BAT | N/A |
| Vascular endothelial growth factor (VEGF) | pg/ml | BAT | Angiogenesis |
| Von Willeband factor (vWF) | IU/ml | BAT | N/A | resulting clusters would be similar to each other, and hence contain redundant biological information about patients, the inventors subsequently used one biomarker from each cluster for the classification of individual patient clusters and patient subpopulations, as described in the next section.

Random Forest Classification (RFC)

As the classification method the inventors used Random Forest Classifier (RFC). Briefly, a RFC is an ensemble method consisting of multiple decision trees which, taken together, can be used to assign each patient into either of two categories on the basis of individual biomarker profiles[19, 20]. Each RFC was constructed using one biomarker from each of the seven biomarker clusters. On the assumption that sub-populations with similar contributory biomarkers are more homogeneous than sub-populations with remarkably different contributory biomarkers, the inventors compared contributory biomarkers across the three largest patient clusters and across patient sub-populations split on basis of clinical information.

As a benchmark, the inventors first determined the classification error and the area under the receiver operating characteristic (AUROC) of RFCs with 1000 trees for all possible collectives of biomarkers for the 157 haematuria patients. The inventors estimated the AUROC by using out-of-bag samples, which means that the trees of a RFC are trained with bootstrap data which omit approximately one-third of the cases each time a tree is trained. These samples, called out-of-bag samples, are used as test data sets to estimate the classification errors[19].

Next, the inventors compared the biomarkers that contributed to RFCs across the three largest patient clusters. Finally, they determined classification errors and AUROCs of RFCs for 14 clinically defined subpopulations of patients. For example, they compared the biomarkers that contributed to the RFC for the 101 smokers to the biomarkers that contributed to the RFC for the 56 non-smokers. Similarly, they compared biomarkers across gender, history of stone disease, history of BPE, anti-hypertensive medication, anti-platelet medication, and anti-ulcer medication.

Results and Discussion:

Non-Random Distribution of Final Diagnoses Across Patient Clusters

Clustering the patients on the basis of their individual patient biomarker profiles resulted in five patient clusters (see FIG. 1). When the inventors matched the clinical data to the patients they observed that the final diagnoses were non-randomly distributed across the patient clusters (see FIG. 2A).

Non-Random Distribution of Cancer-Risk Characteristics Across Patient Clusters

Figure 2:
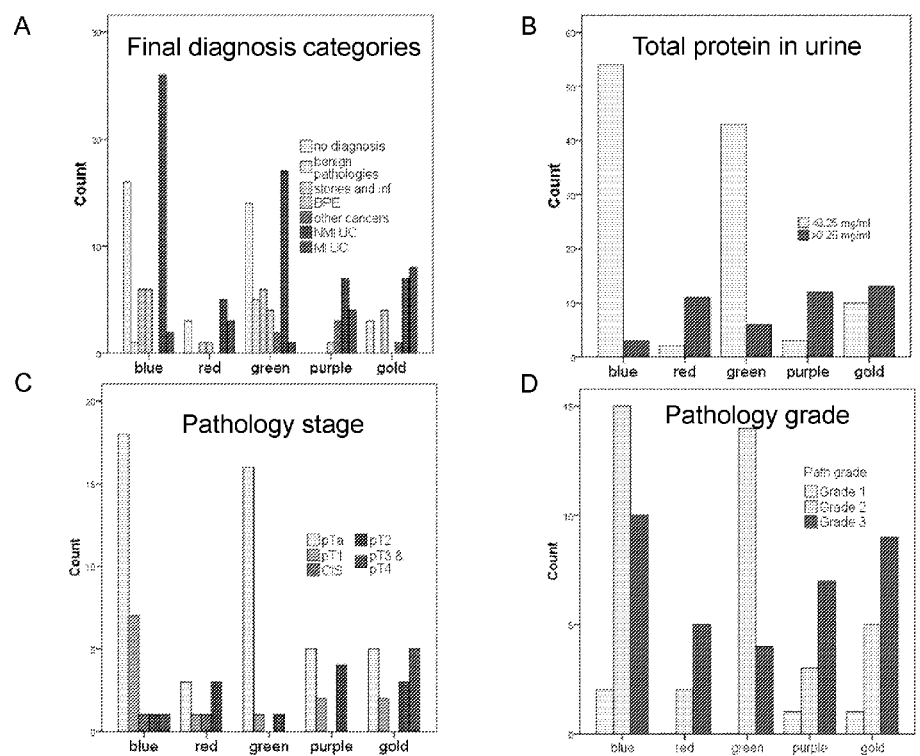
FIG. 2 (A-D) show cancer-risk characteristics across the patient clusters.

Furthermore, the inventors observed that the red, purple and gold patient clusters shown in FIG. 1, were enriched with patients with known cancer-risk characteristics[2, 4, 21] and that the blue and green patient clusters were enriched with patients with non-cancer characteristics (FIG. 2). On the basis of these observations they designated the red, purple and gold natural patient clusters as "high-risk" and the blue and green patient clusters as "low-risk".

Prior to Chi-Square analyses they grouped the "no diagnosis", "benign pathologies", "stones and inflammation" and "BPE" categories together as non-life threatening diagnoses. Similarly, they grouped the cancer patients i.e., "other cancers", "NMI UC" and "MI UC" together as life threatening diagnoses (Table 1). There was a significant difference in life threatening diagnoses between low and high-risk patient clusters (45.3% vs 74.5%, P=0.001). In addition, there were significant differences in proteinuria (8.5% vs 70.6%, P<0.001); and MI UC (6.5% vs 44.1%, P=0.001); grade 3 UC (31.1% vs 63.6%, P=0.006) and malignant cytology (14.1% vs 48.9%, P=0.001) between low and high-risk patient clusters (FIG. 2).

In FIG. 2, the lighter bars represent low risk characteristics, i.e., "no diagnosis", "benign pathology", "<0.25 mg/ml total urinary protein", "pTa stage UC" and "grades 1 and 2 UC". In contrast, the darker bars represent high risk characteristics i.e., "other cancers", "NMI UC", "MI UC", "proteinuria", "≥pT2 stage UC" and "Grade 3 UC". The majority of bars in the blue and green patient clusters were lighter. In contrast, the lighter bars were infrequent in the red, purple and gold patient clusters.

In FIG. 2A, 30/106 (28%) and 43/106 (41%) of patients in the blue and green low-risk patient clusters had a final diagnosis of "no diagnosis" (light bars) and NMI UC (dark bars), respectively. In contrast, in the high-risk patient clusters, 15/51 (29%) of patients were in the "MI UC" final diagnosis category (dark bars) (FIG. 2A). It was notable that 30/36 patients with a final diagnosis of "no diagnosis" clustered within the low-risk patient clusters. It is possible that the six remaining patients with a final diagnosis of "no diagnosis" in the high-risk patient clusters could have undetected serious disease e.g., kidney disease[22, 23] or another cancer. Unfortunately, the inventors could not explore this possibility because they did not have ethical approval to follow-up the patients.

In FIG. 2B, 97/106 (92%) of the patients in the low-risk patient clusters had normal urinary protein the levels (lighter bars). In contrast in the high-risk clusters, 36/51 (71%) of the patients had proteinuria (darker bars) (FIG. 2B). Ideally haematuric patients with significant proteinuria should be referred to nephrology[21] because they may have kidney disease[21-23].

In FIG. 2C pathology stages are represented by bars from left to right i.e., starting with pTa (lighter bars) and progressing through to pT3 and pT4 UC (combined) (darker bars). Although 28 patients within the low-risk blue cluster and 18 patients in the low-risk green cluster had UC, 18/28 (64%) and 16/18 (89%) of these cancers, respectively were stage pTa (lighter bars) (FIG. 2C). Further, 15/18 (73%) of pTa tumours in the blue cluster and 14/16 (88%) of pTa tumours in the green cluster were ≤pTaG2 i.e., very low risk tumours[2]. Forty-seven percent i.e., 15/34 (44%) of the UC patients in the red, purple and gold clusters had tumours ≥pT2, which would be deemed high risk[4] (dark bars) (FIG. 2C).

As discussed above, there is molecular heterogeneity within the same tumour stage and it is possible that some of the pT1 and CIS tumours falling within the red, purple and gold clusters could have predisposing molecular profiles for progression. Furthermore, when the inventors explored the pathological grades of the UC tumours, 21/33 (64%) of the UC patients in the high-risk patient clusters had grade 3 disease (darker bars) compared to 14/45 (31%) in the low-risk clusters (FIG. 2D). In addition, the inventors found that there were significant differences in malignant cytology (14.1% vs 48.9%, P=0.001) between low and high-risk clusters.

Biomarkers Contributing to UC Diagnostic Classifiers for the Low-Risk Patient Clusters were Remarkably Similar To facilitate the classification of patient clusters and clinically split patient sub-populations, the inventors first determined the most informative set of biomarkers for use as feature vectors for UC diagnostic classifiers. Hierarchical clustering identified seven clusters consisting of Nb=(2, 2, 6, 5, 4, 3, 7) biomarkers. It was assumed, in the context of these analyses, that biomarkers within individual clusters would contain redundant biological information about the patients and that it was sufficient to select one biomarker to represent each cluster. Overall, this provided the inventors with a systematic way to estimate the number of representative biomarkers, which can be considered as the effective dimension of the biomarker-space.

From this $N_C = \pi^7_{i=1} N_b(i) = 10080$ combinations can be obtained, each corresponding to a 7-tuple of biomarkers. Hence, the grouping of biomarkers into seven groups broke down the combinatorial complexity of the overall problem, allowing us to conduct an exhaustive search in this constraint set of biomarkers. In contrast, an unconstrained, exhaustive search would not have been feasible because the number of unconstrained feature combinations for up-to 7-dimensional feature vectors is larger than 2.1 million, as given by:

$$N_T 29 = {}^{29}_{k=1}(29/k)$$

(29/k) is the binomial coefficient. This is more than two orders of magnitude larger than $N_C$ making an exhaustive search computationally infeasible.

For all possible $N_C = 10,080$ biomarker combinations, the inventors determined the classification error and the AUROC of RFCs for each of the following:
(1) the 157 patients;
(2) the three largest patient clusters from FIG. 1; and
(3) 14 clinical subpopulations.
Only two of the patient clusters, those designated herein "blue" and "green" (see FIG. 1) contained sufficient numbers i.e., 57 and 48, to train a RFC. However, for reasons of comparison, we also trained a RFC for a cluster designated "gold" herein, which contained 23 patients, 15 of whom were diagnosed with UC (FIG. 1). We found that 4/7 biomarkers were the same in the diagnostic classifiers for the blue and green patient clusters suggesting that these patient clusters had biological similarities. This is interesting because the inventors had previously designated patients within both of these clusters as low-risk.

Furthermore, only 2/7 and 1/7 of the biomarkers, which contributed to the blue and green low-risk clusters, respectively, also contributed to the classifier for the gold cluster. This would suggest that the gold patient cluster has significantly different underlying biological properties in comparison to the blue and green clusters. These observations would concur with our risk stratification hypothesis. The standard deviation of the classification error and of the AUROC for this smaller gold cluster, in comparison to the blue and green patient clusters, increased by 30% (Table 3).

Biomarkers Contributing to UC Diagnostic Classifiers Across Clinically Split Patient Subpopulations were Remarkably Different When the inventors determined classification errors and AUROCs of UC diagnostic RFCs for 14 clinically defined subpopulations we observed the highest AUROC=0.843 (averaged over 100 repetitions) in the classifier for patients not taking anti-platelet medication (n=118). For the clinically split subpopulations, they found that when specific biomarkers contributed to the UC diagnostic RFC for one clinically relevant sub-population, they were less likely to contribute to the RFC for the complementary sub-population. For example, the biomarkers contributing to the UC diagnostic RFC for patients on anti-platelet medication and the biomarkers contributing to the UC diagnostic RFC for patients not prescribed anti-platelet medication, had only two common biomarkers (see Table 3).

TABLE 3

| Variable description | Sub-populations | Biomarkers | Classification error (SD) | AUROC (SD) |
| --- | --- | --- | --- | --- |
| All 157 haematuria patients | Controls n = 77 UC n = 80 | CRP, EGF, IL-6, IL-1α, MMP9NGAL, osmolarity, CEA | 0.203 (0.017) | 0.766 (0.152) |
| Patient clusters # | Blue n = 57 (28) | TNFα, EGF, NSE, NGAL, MMP9NGAL, TM, FAS | 0.155 (0.029) | 0.800 (0.258) |
| | Green n = 49 (18) | TNFα, EGF, IL-6, IL-1α, MMP9NGAL, TM, CEA | 0.204 (0.037) | 0.825 (0.264) |
| | Gold n = 23 (15) | CRP, sTNFR1, vWF, IL-1α, MMP9NGAL, creatinine, BTA | 0.245 (0.049) | 0.700 (0.349) |
| Clinical sub-populations: | | | | |
| Smoking | Smokers n = 101 (60) | CRP, EGF, MMP9, IL-1α, IL-4, TM, IL-2 | 0.276 (0.027) | 0.770 (0.117) |
| | Non-smokers n = 56 (20) | TNFα, sTNFR1, IL-6, IL-1α, MMP9NGAL, creatinine, CEA | 0.156 (0.027) | 0.783 (0.159) |
| Gender | Males n = 120 (65) | CRP, EGF, CK18, IL-β, IL-8, creatinine, IL-2 | 0.272 (0.030) | 0.753 (0.117) |
| | Females n = 37 (15) | CRP, EGF, IL-6, dDimer, MMP9NGAL, osmolarity, CEA | 0.181 (0.054) | 0.830 (0.146) |
| Hx stone disease | Yes n = 30 (14) | CRP, sTNFR1, CK18, IL-1α, IL-8, creatinine, VEGF | 0.322 (0.062) | 0.738 (0.194) |
| | No n = 127 (66) | CRP, EGF, IL-6, IL-1α, MMP9NGAL, creatinine, CEA | 0.186 (0.015) | 0.817 (0.117) |

TABLE 3-continued

| Variable description | Sub-populations | Biomarkers | Classification error (SD) | AUROC (SD) |
|---|---|---|---|---|
| Hx BPE | Yes n = 30 (14) | CRP, EGF, IL-6, IL-1α, MMP9NGAL, TM, CEA | 0.192 (0.018) | 0.826 (0.148) |
|  | No n = 127 (66) | CRP, EGF, CK18, NGAL, MMP9NGAL, creatinine, BTA | 0.266 (0.061) | 0.788 (0.169) |
| Anti-hypertensive medication | On medication n = 73 (51) | TNFα, EGF, IL-6, protein, MMP9NGAL, creatinine, CEA | 0.211 (0.025) | 0.731 (0.161) |
|  | No medication n = 83 (28) | TNFα, STNFR1, IL-6, NGAL, IL-8, TM, CEA | 0.145 (0.028) | 0.810 (0.132) |
| Anti-platelet medication | On medication n = 37 (25) | TNFα, EGF, IL-6, protein, IL-8, osmolarity, CEA | 0.215 (0.019) | 0.780 (0.141) |
|  | No medication n = 118 (53) | CRP, EGF, MCP-1, protein, MMP9NGAL, TM, FPSA | 0.160 (0.046) | 0.843 (0.153) |
| Anti-ulcer medication | On medication n = 33 (17) | CRP, EGF, IL-6, IL-1α, IL-8, TM, CEA | 0.220 (0.018) | 0.827 (0.118) |
|  | No medication n = 123 (62) | CRP, EGF, vWF, IL-β, MMP9NGAL, TM, HA | 0.259 (0.072) | 0.812 (0.168) |

Biomarkers Associated with Inflammatory Conditions Predominated Two of the Biomarker Clusters Biomarkers associated with inflammatory conditions predominated the biomarker clusters termed herein "black" and "gold". The black cluster contained CRP and TNFα. The gold cluster comprised d-Dimer, IL-1α, IL-1β, NGAL and total protein. The latter five biomarkers were significantly elevated in urine from patients in the high-risk patient clusters (Mann Whitney U, P<0.001) (see Table 4). The median and inter-quartile range of each biomarker in each patient cluster is shown in Table 4.

TABLE 4

| Biomarker (units) | Median (inter-quartile range) in patient clusters | | | | |
|---|---|---|---|---|---|
|  | Blue | Red | Green | Purple | Gold |
| BLACK CLUSTER | | | | | |
| CRP (ng/ml) | 1.05 (0.74 to 1.33) | 0.86 (<0.67 to 0.91) | 1.06 (0.84 to 1.25) | <0.67 (<0.67 to 0.83) | 0.75 (<0.67 to 0.90) |
| TNFα (pg/ml) | 10.52 (7.78 to 13.25) | 9.07 (7.36 to 9.79) | 9.54 (7.46 to 11.78) | 11.66 (8.95 to 15.48) | 10.20 (8.31 to 12.820) |
| GREEN CLUSTER | | | | | |
| EGF (pg/ml) | 7056 (4965 to 13752) | 3633 (1874 to 5992) | 6477 (2784 to 10943) | 3722.33 (3058 to 4956) | 13826 (9488 to 20332) |
| sTNFR1 (pg/ml) | 0.67 (0.41 to 1.04) | 0.75 (0.47 to 1.05) | 0.57 (0.24 to 1.61) | 0.74 (0.45 to 1.06) | 1.60 (0.97 to 2.54) |
| PURPLE CLUSTER | | | | | |
| CK18 (ng/ml) | 2.30 (0.71 to 3.59) | 1.22 (0.42 to 2.78) | 2.03 (0.75 to 4.33) | 8.97 (2.88 to 21.43) | 6.43 (2.67 to 10.28) |
| MCP-1 (pg/ml) | 112 (38 to 212) | 73 (41 to 141) | 67 (28 to 113) | 269 (118 to 871) | 237 (106 to 550) |
| NSE (ng/ml) | IQR below LOD | 0.28 (<0.26 to 0.92) | IQR below LOD | 1.72 (<0.26 to 18.32) | 0.51 (< 0.26 to 2.37) |
| MMP-9 (ng/ml) | IQR below LOD | IQR below LOD | IQR below LOD | 15.15 (6.57 to 50.81) | IQR below LOD |
| IL-6 (pg/ml) | 1.37 (<1.20 to 3.60) | 12.93 (3.27 to 26.67) | <1.20(<1.20 to 2.50) | 194.33 (16.43 to 577.33) | 40.80 (4.80 to 196.67) |
| vWF (IU/ml) | 0.01 (0.01 to 0.02) | 0.01 (0.00 to 0.01) | 0.01 (0.01 to 0.01) | 0.01 (0.01 to 0.02) | 0.01 (0.01 to 0.03) |
| GOLD CLUSTER | | | | | |
| Protein (mg/ml) | 0.07 (0.05 to 0.11) | 0.44(0.29 to 0.60) | 0.08 (0.05 to 0.12) | 0.59 (0.25 to 0.93) | 0.30 (0.09 to 1.00) |
| NGAL (ng/ml) | 123 (92 to 212) | 192 (146 to 297) | 110 (74 to 148) | 1379 (602 to 1922) | 464 (108 to 1368) |
| dDimer (ng/ml) | <2.10 (<2.10 to 5.02) | 47.01 (11.80 to 138.27) | <2.10 (<2.10 to 3.62) | 638.69 (62.44 to 145.33) | 58.35 (<2.10 to 559.38) |

TABLE 4-continued

| Biomarker (units) | Median (inter-quartile range) in patient clusters | | | | |
|---|---|---|---|---|---|
| | Blue | Red | Green | Purple | Gold |
| IL-1α (pg/ml) | 0.90 (0.90 to 2.52) | 2.42 (1.01 to 3.53) | 0.90 (0.90 to 1.01) | 21.35 (5.80 to 30.93) | 2.47 (0.90 to 81.00) |
| IL-1β (pg/ml) | IQR below LOD | IQR below LOD | IQR below LOD | 17.80 (5.46 to 78.87) | <1.60 (<1.60 to 19.12) |
| PINK CLUSTER | | | | | |
| IL-8 (pg/ml) | 32.40 (7.93 to 265.83) | 292.67 (117.33 to 604.33) | 28.63 (7.90 to 135.33) | 2900 (2064 to 2900) | 875.67 (48.40 to 2900) |
| MMP9NGAL | 0.09 (0.08 to 0.10) | 0.16 (0.10 to 0.29) | 0.07 (0.07 to 0.09) | 0.29 (0.23 to 0.48) | 0.23 (0.09 to 0.29) |
| IL-4 (pg/ml) | IQR below LOD | IQR below LOD | IQR below LOD | <6.60 (<6.60 to 6.80) | IQR below LOD |
| sTNFR2 (pg/ml) | IQR below LOD | <0.15 (<0.15 to 0.26) | <0.15 (<0.15 to 0.26) | IQR below LOD | <0.15 (<0.15 to 0.61) |
| BLUE CLUSTER | | | | | |
| Creatinine (μmol/L) | 9608 (7961 to 13360) | 5605 (4454 to 11945) | 7115 (3868 (12595) | 7600 (5360 to 8625) | 14087 (12405 to 17245) |
| Osmolarity (mOsm) | 536 (450 to 741) | 462 (276 to 560) | 526 (278 to 675) | 404 (314 to 482) | 644 (567 to 7840) |
| TM (ng/ml) | 4.08 (3.19 to 4.97) | 3.97 (1.55 to 5.69) | 4.00 (1.74 to 5.68) | 3.49 (2.65 to 4.00) | 6.30 (5.34 to 8.86) |
| YELLOW CLUSTER | | | | | |
| IL-2 (pg/ml) | 5.61 (5.21 to 5.92) | 5.24 (5.02 to 5.65) | 5.45 (5.20 to 6.27) | 6.89 (5.99 to 7.24) | 5.99 (5.65 to 7.20) |
| CEA (ng/ml) | 1.57 (1.16 to 2.58) | 1.59 (1.15 to 3.23) | 1.36 (0.87 to 2.10) | 1.77 (1.30 to 2.39) | 1.37 (0.89 to 2.80) |
| HA (ng/ml) | 685 (439 to 866) | 835 (595 to 1005) | 594 (282 to 900) | 1569 (1143 to 1846) | 1258 (883 to 1712) |
| FPSA (ng/ml) | 0.09 (0.04 to 0.21) | 0.05 (0.04 to 0.23) | 0.07 (0.04 to 0.12) | 0.13 (0.07 to 0.30) | 0.05 (0.04 to 0.10) |
| BTA (U/ml) | 8.52 (2.57 to 38.96) | 248.01 (206.82 to 394.15) | 6.27 (1.21 to 17.92) | 278.41 (226.40 to 504.33) | 213.00 (15.24 to 476.28) |
| VEGF (ng/ml) | 88 (37 to 271) | 96 (76 to 220) | 78 (38 to 122) | 1266 (414 to 1500) | 253 (79 to 621) |
| FAS (pg/ml) | 64 (42 to 96) | 83 (60 to 128) | 56 (37 to 86) | 214 (106 to 475) | 200 (96 to 279) |

Translation of Risk and Diagnostic Classifiers from Systems Biology to the Clinic The inventors have described how hierarchical clustering conducted on the basis of individual patient biomarker profiles identified patient clusters and how cancer associated risk characteristics were non-randomly distributed across these clusters (FIGS. 1 and 2 and Tables 5-10). These findings demonstrate that it should be possible to define risk classifiers that could be diagnostic aids during triage for haematuric patients. This approach could have the potential to significantly improve healthcare outcomes for patients with haematuria.

Figure 3:
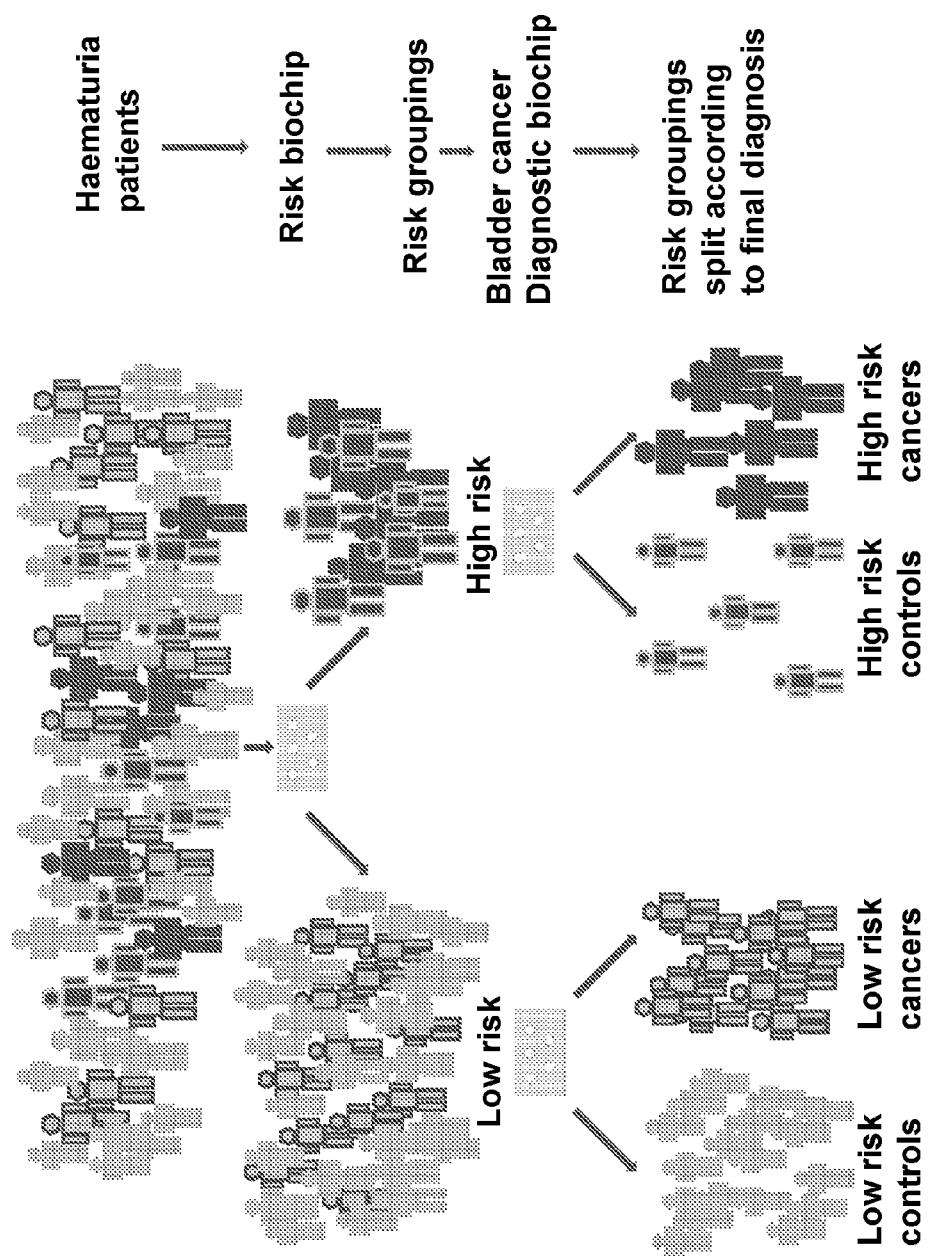
FIG. 3 is a representation of translation of classifiers into biochip format for risk stratification of haematuria patients.

Biochip array technology [17] allows simultaneous measurement of multiple biomarkers and hence could facilitate the translation of protein-based classifiers, as described in this manuscript, from systems biology to the clinic[24]. Antibodies, raised against biomarkers contributing to an individual classifier, can be formatted onto a single biochip. One biochip can produce measurements for multiple proteins in a few hours. Risk biochips and UC diagnostic biochips could be created and validated as risk and diagnostic classifiers, respectively [25]. In clinical practice, scores between 0 and 1, from the risk and diagnostic UC biochips would make it possible to assign each patient with haematuria as a "low-risk control", a "high-risk control", a "low-risk UC" or a "high-risk" UC (FIG. 3). Scores <0.4 obtained using the risk biochip would indicate that the risk of serious disease was low, while a score <0.4 obtained using the UC diagnostic biochip would suggest that it was unlikely that the patient had UC. Similarly, scores >0.6 would indicate a high risk of serious disease, or that the patient could have UC. Scores between 0.4 and 0.6 could be interpreted as indicative of potential risk and the possibility of UC. If specificities and sensitivities for both biochips >90%, this would mean a high-risk cancer patient would have a 1:10 chance of being wrongly classified as low-risk and subsequently a 1:10 chance of being wrongly classified as a control. In this scenario, out of 1000 high-risk cancer patients ~810 would be correctly classified as high-risk cancers, ~90 as high-risk controls, ~90 as low-risk cancers and ~10 as low-risk controls (FIG. 3). Following biochip analyses, patients with scores 0.2 from both biochips and no clinical risk factors, i.e., low-risk controls, could be monitored in primary care. This would lead to a reduction in the number of cystoscopies in these patients. In another scenario, a proportion of patients might be assigned as high-risk control patients following analyses of their samples using the biochips. These patients should be investigated further, because they could have other diseases e.g., kidney disease which could then be managed appropriately [21]. In this way, improved triage would result in expeditious diagnosis for a greater proportion of patients with haematuria who would then receive earlier and more effective therapeutic interventions. This would represent a significant healthcare improvement [26].

CONCLUSIONS

Following clustering based on individual patient biomarker profiles, the inventors identified five patient clusters.

It was observed that the final diagnoses for the 157 patients with haematuria were non-randomly distributed across the patient clusters. Other high-risk characteristics i.e., proteinuria, pathological stage, pathological grade and malignant cytology were also non-randomly distributed across the patient clusters. Indeed, we identified three patient clusters that were enriched with patients with cancer-risk characteristics and two patient clusters that were enriched with patients with non-cancer characteristics. These findings indicate the feasibility of creating risk classifiers for the triage of patients with haematuria. Risk classifiers could improve decision-making at the point of triage ensuring that more patients would receive an accurate diagnosis thereby improving outcome for a greater proportion of patients.

List of Abbreviations

AUROC—area under the receiver operating curve
BPE—benign prostate enlargement
BTA—bladder tumour antigen
CEA—carcino-embryonic antigen
CIS—carcinoma in situ
CK18—cytokeratin 18
IL—interleukin
CRP—C-reactive protein
EGF—epidermal growth factor
FAS—tumour necrosis factor receptor superfamily member 6
FPSA—free prostate specific antigen
TPSA—total prostate specific antigen
HA—hyaluronidase
IQR—inter-quartile range
LOD—limit of detection
MCP1—monocyte chemo-attractant protein-1
MI—muscle invasive
MMP-9—matrix metalloproteinase-9
NGAL—neutrophil-associated gelatinase lipocalin
NMI—non-muscle invasive
NMP22—nuclear matrix protein 22
NSE—neuron specific enolase
PSA—prostate specific antigen
RCC—renal cell carcinoma
RFC—Random Forest Classifiers
ROC—receiver operating curve
TCC—transitional cell carcinoma
TNFα—tumour necrosis factor alpha
sTNFR 1/2—soluble TNFαreceptor 1/2
TM—thrombomodulin
TUP—total urinary protein
UC—urothelial cancer
UTI—urinary tract infection
VEGF—vascular endothelial growth factor
vWF—von Willebrand factor

REFERENCES

1. Mostafid H, Persad R, Kockelbergh R, Fawcett D: "Is it time to re-design the haematuria clinic?" *BJU Int* 2010, 105(5):585-588.
2. Jacobs B L, Lee C T, Montie J E: "Bladder cancer in 2010: how far have we come?" *C A Cancer J Clin* 2010, 60(4):244-272.
3. Jemal A, Bray F, Center M M, Ferlay J, Ward E, Forman D: "Global cancer Statistics" *C A Cancer J Clin* 2011, 61(2):69-90.
4. Kulkarni G S, Finelli A, Fleshner N E, Jewett M A, Lopushinsky S R, Alibhai S M: "Optimal management of high-risk T1G3 bladder cancer: a decision analysis" *PLoS Med* 2007, 4(9):e284.
5. van der Aa M N, Steyerberg E W, Bangma C, van Rhijn B W, Zwarthoff E C, van der Kwast T H: "Cystoscopy revisited as the gold standard for detecting bladder cancer recurrence: diagnostic review bias in the randomized, prospective CEFUB trial" *J Urol* 2010, 183(1):76-80.
6. Lotan Y, Elias K, Svatek R S, Bagrodia A, Nuss G, Moran B, Sagalowsky Al: "Bladder cancer screening in a high risk asymptomatic population using a point of care urine based protein tumor marker" *J Urol* 2009, 182(1):52-57.
7. Kinders R, Jones T, Root R, Bruce C, Murchison H, Corey M, Williams L, Enfield D, Hass G M: "Complement factor H or a related protein is a marker for transitional cell cancer of the bladder" *Clin Cancer Res* 1998, 4(10):2511-2520.
8. Johnston B, Morales A, Emerson L, Lundie M: "Rapid detection of bladder cancer: a comparative study of point of care tests" *J Urol* 1997, 158(6):2098-2101.
9. Abogunrin F, O'Kane H F, Ruddock M W, Stevenson M, Reid C N, O'Sullivan J M, Anderson N H, O'Rourke D, Duggan B, Lamont J V, Boyd R E, Hamilton P, Nambirajan T, Williamson K E: "The impact of biomarkers in multivariate algorithms for bladder cancer diagnosis in patients with hematuria" *Cancer* 2012, 118(10):2641-50.
10. Leibovici D, Grossman H B, Dinney C P, Millikan R E, Lerner S, Wang Y, Gu J, Dong Q, Wu X: "Polymorphisms in inflammation genes and bladder cancer: from initiation to recurrence, progression, and survival" *J Clin Oncol* 2005, 23(24):5746-5756.
11. Margel D, Pesvner-Fischer M, Baniel J, Yossepowitch O, Cohen I R: "Stress proteins and cytokines are urinary biomarkers for diagnosis and staging of bladder cancer" *Eur Urol* 2011, 59(1):113-119.
12. Vidal M: "A unifying view of 21st century systems biology" *FEBS Lett* 2009, 583(24):3891-3894.
13. Emmert-Streib F, Glazko G V: "Network biology: a direct approach to study biological function" Wiley Interdiscip Rev Syst Biol Med 2011, 3(4):379-391.
14. Bossuyt P M, Reitsma J B, Bruns D E, Gatsonis C A, Glasziou P P, Irwig L M, Lijmer J G, Moher D, Rennie D, de Vet H C, Standards for Reporting of Diagnostic Accuracy: "Towards complete and accurate reporting of studies of diagnostic accuracy: the STARD initiative. Standards for Reporting of Diagnostic Accuracy" *Clin Chem* 2003, 49(1):1-6.
15. Bossuyt P M, Reitsma J B, Bruns D E, Gatsonis C A, Glasziou P P, Irwig L M, Moher D, Rennie D, de Vet H C, Lijmer J G, Standards for Reporting of Diagnostic Accuracy: "The STARD statement for reporting studies of diagnostic accuracy: explanation and elaboration" *Clin Chem* 2003, 49(1):7-18.
16. Barratt J, Topham P: "Urine proteomics: the present and future of measuring urinary protein components in disease" *CMAJ* 2007, 177(4):361-368.
17. Fitzgerald S P, Lamont J V, McConnell R I, Benchikh el O: "Development of a high-throughput automated analyzer using biochip array technology" *Clin Chem* 2005, 51(7):1165-1176.
18. Theodoridis S: Pattern recognition: 2nd ed. Amsterdam London: Academic Press; 2003.
19. Breiman L. "Bagging Predictors" *Machine Learning* 1996, 24(2):123-140.

20. Zhang H and Singer B H. *Recursive partitioning and applications*. New York: Springer; 2010.
21. http://www.baus.org.uk/AboutBAUS/publications/haematuria-guidelinesNICE guidelines.
22. Fassett R G, Venuthurupalli S K, Gobe G C, Coombes J S, Cooper M A, Hoy W E: "Biomarkers in chronic kidney disease: a review" Kidney Int 2011, 80(8):806-821.
23. Goldstein S L: "Acute kidney injury biomarkers: renal angina and the need for a renal troponin I" *BMC Med* 2011, 9:135.
24. McShane L M: "Statistical challenges in the development and evaluation of marker-based clinical tests" *BMC Medicine* 2012, 10:52.
25. Marchio C, Dowsett M, Reis-Filho J S: "Revisiting the technical validation of tumour biomarker assays: how to open a Pandora's box" *BMC Medicine* 2011, 9:41
26. Ferrante di Ruffano L, Hyde C J, McCaffery K J, Bossuyt P M, Deeks J J: "Assessing the value of diagnostic tests: a framework for designing and evaluating trials" *BMJ* 2012, 344:e686.
27. Liu E T: *Systems Biomedicine*: Boston: Academic Press; 2010.

We claim:

1. A method of defining the likelihood of a subject having bladder cancer, comprising the steps of:
  (A) assessing the subject's likelihood of having bladder cancer by:
    i. identifying at least one sub-population group appropriate to the subject;
    ii. measuring the protein concentration level of one or more biomarkers selected according to the sub-population group in a sample obtained from the subject, wherein said measuring comprises contacting the sample with a substrate having at least one antibody against each of the one or more biomarkers on the substrate;
    iii. inputting one or more values into an algorithm to produce an output value, wherein the one or more inputted values are representative of the measured protein concentration level of the one or more biomarkers, and wherein the algorithm carries out ROC statistical analysis and/or logistical regression; and
    iv. correlating the output value with the likelihood of the subject having bladder cancer,
  wherein the sub-population group is selected according to smoking habits, gender, presence/absence of stone disease, history of benign prostate enlargement (BPE) or prescription of anti-hypertensive, anti-platelet and/or anti-ulcer medication, and
  (B) determining the subject's stratified risk level of serious disease by:
    v. measuring the protein concentration level of one or more biomarkers specific for one or more risk classifiers defined using Random Forest Classifiers (RFC), logistic regression or another appropriate systems biology or statistical approach in a sample obtained from the subject, wherein said measuring comprises contacting the sample with a substrate having at least one antibody against each of the one or more biomarkers on the substrate,
    vi. inputting one or more values into an algorithm or algorithms to produce an output value, wherein the one or more inputted values are representative of the measured protein concentration level of the one or more biomarkers, and wherein the one or more algorithms carry out ROC statistical analysis and/or logistical regression; and
    vii. correlating the output value with a stratified risk level of underlying serious disease,
  wherein the likelihood of having bladder cancer is combined with the stratified risk level of having serious disease, wherein the risk of having bladder cancer and/or serious disease is categorized as: high-risk bladder cancer requiring immediate cystoscopy; low-risk bladder cancer requiring urgent cystoscopy; high-risk control requiring close evaluation and further investigation; or low-risk control requiring primary care monitoring, and wherein:
    if the smoker sub-population is selected, the protein concentration level of the biomarkers CRP, EGF, MMP9, IL-1α, IL-4, TM and IL-2 is measured in step (ii);
    if the non-smoker sub-population is selected, the protein concentration level of the biomarkers TNFα, sTNFR1, IL-6, IL-1α, MMP9/NGAL complex and CEA is measured in step (ii) and the creatinine protein concentration level in the sample is also measured;
    if the gender sub-population is selected and the subject is male, the protein concentration level of the biomarkers CRP, EGF, CK18, IL-1β, IL-8 and IL-2 is measured in step (ii) and the creatinine protein concentration level in the sample is also measured;
    if the gender sub-population is selected and the subject is female, the protein concentration level of the biomarkers CRP, EGF, IL-6, dDimer, MMP9/NGAL complex and CEA is measured in step (ii) and the osmolarity of the sample is also measured;
    if the stone disease sub-population is selected and the subject is positive for stone disease, the protein concentration level of the biomarkers CRP, sTNFR1, CK18, IL-1α, IL-8 and VEGF is measured in step (ii) and the creatinine protein concentration level in the sample is also measured;
    if the stone disease sub-population is selected and the subject is negative for stone disease, the protein concentration level of the biomarkers CRP, EGF, IL-6, IL-1α, MMP9/NGAL complex and CEA is measured in step (ii) and the creatinine protein concentration level in the sample is also measured;
    if the BPE sub-population is selected and the subject is positive for BPE, the protein concentration level of the biomarkers CRP, EGF, IL-6, IL-1α, MMP9/NGAL complex, TM and CEA is measured in step (ii);
    if the BPE sub-population is selected and the subject is negative for PBE, the protein concentration level of the biomarkers CRP, EGF, CK18, NGAL, MMP9/NGAL complex and BTA is measured in step (ii) and the creatinine protein concentration level in the sample is also measured;
    if the anti-hypertensive medication sub-population is selected and the subject is positive for anti-hypertensive medication, the protein concentration level of the biomarkers TNFα, EGF, IL-6, MMP9/NGAL complex and CEA is measured in step (ii) and the creatinine protein concentration level and total protein level in the sample is also measured;
    if the anti-hypertensive medication sub-population is selected and the subject is negative for anti-hypertensive medication, the protein concentration level of the biomarkers TNFα, sTNFR1, IL-6, NGAL, IL-8, TM and CEA is measured in step (ii);

if the anti-platelet medication sub-population is selected and the subject is positive for anti-platelet medication, the protein concentration level of the biomarkers TNFα, EGF, IL-6, IL-8 and CEA is measured in step (ii) and the total protein level and osmolarity of the sample is also measured;

if the anti-platelet medication sub-population is selected and the subject is negative for anti-platelet medication, the protein concentration level of the biomarkers CRP, EGF, MCP-1, MMP9/NGAL complex, TM and FPSA is measured in step (ii) and the total protein level of the sample is also measured;

if the anti-ulcer medication sub-population is selected and the subject is positive for anti-ulcer medication, the protein concentration level of the biomarkers CRP, EGF, IL-6, IL-1α, IL-8, TM and CEA is measured in step (ii); and if the anti-ulcer medication sub-population is selected and the subject is negative for anti-ulcer medication, the protein concentration level of the biomarkers CRP, EGF, vWF, IL-1β, MMP9/NGAL complex, TM and HA is measured in step (ii).

2. The method according to claim 1, wherein the subject is a patient presenting with haematuria.

3. The method according to claim 1, wherein the bladder cancer is urothelial carcinoma (UC).

4. The method according to claim 1, wherein the sample is selected from the group consisting of urine, blood, plasma and serum.

5. The method according to claim 1, wherein the biomarkers in (A) and (B) are selected from the list comprising: CRP; EGF; IL-6; IL-1α; MMP9; IL-4; TM; IL-2; TNFα; sTNFR1; sTNFR2; MMP9/NGAL complex; CEA; CK18; IL-1β; IL-8; dDimer; VEGF; NGAL; BTA; FPSA; vWF; HA; NSE; MCP1; NMP22; TPSA; and FAS.

6. The method according to claim 5, wherein TPSA, FPSA and CEA are measured in a serum sample.

7. The method according to claim 5, wherein CRP; EGF; IL-6; IL-1α; MMP9; IL-4; TM; IL-2; TNFα; sTNFR1; sTNFR2; MMP9/NGAL complex; CK18; IL-1β; IL-8; dDimer; VEGF; NGAL; BTA; vWF; HA; NSE; MCP1; NMP22; and FAS are measured in a urine sample.

8. The method according to claim 1, wherein osmolarity level, total urinary protein (TUP) level and/or creatinine protein concentration level in the sample are also measured and the value(s) included in the algorithms.

9. The method according to claim 1, wherein the method is carried out two or more times for each individual subject by selecting two or more sub-population groups appropriate to the subject and measuring the protein concentration level of one or more biomarkers selected according to the sub-population groups.

10. The method according to claim 1, further comprising a diagnostic step(s) of determining whether the subject is at high or low-risk of bladder cancer, comprising measuring the protein concentration level of one or more bladder cancer markers selected from BTA, CEA TM, NMP22, EGF, TNFα, NSE, NGAL, MMP9/NGAL complex, FAS, IL-6, IL-α, CRP, sTNFR1, sTNFR2, vWF, IL-1β, MCP-1, HA, CK18, VEGF, IL-8, IL-2, d-Dimer, MMP-9, IL-4, TPSA, FPSA and TUP.

11. The method according to claim 10, wherein the diagnostic steps comprise:

assaying the sample from the subject for the protein concentration levels of at least one combination of biomarkers selected from the combination of i) BTA, CEA and TM, and the combination of ii) NMP22 and EGF, wherein the protein concentration levels of the at least one combination of biomarkers is assayed by contacting the sample with a substrate having at least one antibody against each of the biomarkers included in the at least one combination of biomarkers;

providing the results of the assay for the protein concentration levels of the at least one combination of biomarkers;

wherein an increase in protein concentration levels of the biomarkers in combination i) or an increase in the protein concentration level of NMP22 and a decrease in the protein concentration level of EGF in combination ii) compared to a control value indicates bladder cancer in the subject.

12. The method according to claim 10, wherein the diagnostic step comprises:

detecting the presence of at least two biomarkers selected from CEA, VEGF, IL-8, NGAL, NSE, IL-2, EGF, TM, d-Dimer, MMP-9, IL-6, IL-4, MMP-9/NGAL complex, FAS, CRP, TUP and NMP22 in one or more samples isolated from the subject, wherein the presence of a combination of at least two of the biomarkers in the one or more samples indicates the presence or risk of bladder cancer.

13. The method according to claim 10, wherein the diagnostic step comprises:

measuring the protein concentration level of one or more biomarkers in a sample obtained from the subject selected from the groups (1) TNFα, EGF, NSE, NGAL, MMP9/NGAL, TM and FAS;

(2) TNFα, EGF, IL-6, IL-1α, MMP9/NGAL, TM and CEA; or (3) CRP, sTNFR1, vWF, IL-1α, MMP9/NGAL and BTA according to the sub-population group in a sample obtained from the subject;

inputting one or more values into a ROC statistical analysis to obtain a AUROC value, wherein the one or more inputted values are representative of the measured protein concentration level of the one or more biomarkers; and correlating the AUROC value with a high or low risk of developing bladder cancer, wherein if the biomarkers of group (3) are selected, creatinine protein concentration levels in the sample are also measured and the value(s) included in the ROC statistical analysis.

14. The method of claim 1, wherein the risk of having bladder cancer and/or serious disease is categorized as high-risk or low-risk bladder cancer, and said method further comprises subsequently conducting cystoscopy on the subject.

15. The method of claim 1, further comprising administering an agent to the subject that is known to treat or prevent bladder cancer.

16. The method of claim 1, wherein the at least one antibody on the substrate comprises a monoclonal antibody.

17. A method of assessing biomarkers in a subject based on a subpopulation to which the subject belongs, comprising measuring the protein concentration level of a combination of biomarkers in a sample obtained from the subject, wherein said measuring comprises contacting the sample with a substrate having at least one antibody against each of the combination of biomarkers on the substrate, inputting each of the biomarker values into an algorithm to produce an output value, wherein the one or more inputted values are representative of the measured protein concentration level of the combination of biomarkers, and wherein the algorithm carries out ROC statistical analysis and/or logistical regression, wherein:

- the subject is a smoker, and the level of the biomarkers CRP, EGF, MMP9, IL-1α, IL-4, TM and IL-2 is measured; or
- the subject is a non-smoker, the level of the biomarkers TNFα, sTNFR1, IL-6, IL-1α, MMP9/NGAL complex and CEA is measured, and the creatinine level in the sample is also measured; or
- the subject is male, the level of the biomarkers CRP, EGF, CK18, IL-1β, IL-8 and IL-2 is measured, and the creatinine level in the sample is also measured; or
- the subject is female, the level of the biomarkers CRP, EGF, IL-6, dDimer, MMP9/NGAL complex and CEA is measured, and the osmolarity of the sample is also measured; or
- the subject is positive for stone disease, the level of the biomarkers CRP, sTNFR1, CK18, IL-1α, IL-8 and VEGF is measured, and the creatinine level in the sample is also measured; or
- the subject is negative for stone disease, the level of the biomarkers CRP, EGF, IL-6, IL-1α, MMP9/NGAL complex and CEA is measured, and the creatinine level in the sample is also measured; or
- the subject is positive for BPE, and the level of the biomarkers CRP, EGF, IL-6, IL-1α, MMP9/NGAL complex, TM and CEA is measured; or
- the subject is negative for PBE, the level of the biomarkers CRP, EGF, CK18, NGAL, MMP9/NGAL complex and BTA is measured, and the creatinine level in the sample is also measured; or
- the subject is positive for anti-hypertensive medication, the level of the biomarkers TNFα, EGF, IL-6, MMP9/NGAL complex and CEA is measured, and the creatinine level and total protein level in the sample is also measured; or
- the subject is negative for anti-hypertensive medication, and the level of the biomarkers TNFα, sTNFR1, IL-6, NGAL, IL-8, TM and CEA is measured; or
- the subject is positive for anti-platelet medication, the level of the biomarkers TNFα, EGF, IL-6, IL-8 and CEA is measured, and the total protein level and osmolarity of the sample is also measured; or
- the subject is negative for anti-platelet medication, the level of the biomarkers CRP, EGF, MCP-1, MMP9/NGAL complex, TM and FPSA is measured, and the total protein level of the sample is also measured; or
- the subject is positive for anti-ulcer medication, and the level of the biomarkers CRP, EGF, IL-6, IL-1α, IL-8, TM and CEA is measured; or
- the subject is negative for anti-ulcer medication, and the level of the biomarkers CRP, EGF, vWF, IL-1β, MMP9/NGAL complex, TM and HA is measured.

18. The method of claim 17, wherein the at least one antibody on the substrate comprises a monoclonal antibody.

* * * * *